United States Patent
Cortez et al.

(10) Patent No.: US 9,879,029 B2
(45) Date of Patent: Jan. 30, 2018

(54) ERK INHIBITORS

(71) Applicant: Eli Lilly and Company, Indianapolis, IN (US)

(72) Inventors: Guillermo S. Cortez, Indianapolis, IN (US); Sajan Joseph, Carmel, IN (US); Johnathan Alexander McLean, Indianapolis, IN (US); William Thomas McMillen, Indianapolis, IN (US); Michael John Rodriguez, Indianapolis, IN (US); Gaiying Zhao, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/529,641

(22) PCT Filed: Dec. 15, 2015

(86) PCT No.: PCT/US2015/065672
§ 371 (c)(1),
(2) Date: May 25, 2017

(87) PCT Pub. No.: WO2016/106009
PCT Pub. Date: Jun. 30, 2016

(65) Prior Publication Data
US 2017/0267691 A1  Sep. 21, 2017

Related U.S. Application Data

(60) Provisional application No. 62/095,214, filed on Dec. 22, 2014.

(51) Int. Cl.
*C07D 495/04* (2006.01)
*C07B 59/00* (2006.01)

(52) U.S. Cl.
CPC .......... *C07D 495/04* (2013.01); *C07B 59/002* (2013.01); *C07B 2200/05* (2013.01); *C07B 2200/13* (2013.01)

(58) Field of Classification Search
CPC ...................................... C07D 495/04
USPC ...................................... 546/275.4; 514/338
See application file for complete search history.

(56) References Cited

U.S. PATENT DOCUMENTS 9,469,652 B2   10/2016   Cortez et al.

FOREIGN PATENT DOCUMENTS

WO   2008/153947 A2   12/2008
WO   2013/130976 A1   9/2013

*Primary Examiner* — Patricia L Morris
(74) *Attorney, Agent, or Firm* — Tina M. Tucker; Dannica Hostettler

(57) ABSTRACT

The present invention provides thieno[2,3-c]pyrrol-4-one compounds that inhibit activity of extracellular-signal-regulated kinase (ERK) and may be useful in the treatment of cancer.

12 Claims, No Drawings

ERK INHIBITORS

The present invention relates to thieno[2,3-c]pyrrol-4-one compounds, or pharmaceutically acceptable salts thereof, and pharmaceutical compositions comprising the compounds, that inhibit activity of extracellular-signal-regulated kinase (ERK) and may be useful for treating cancer.

The ERK/MAPK pathway is important for cell proliferation and frequently observed to be activated in many tumors. Ras genes, which are upstream of ERK1/2, are mutated in several cancers including colorectal, melanoma, non-small cell lung cancer as well as breast and pancreatic tumors. High Ras activity is accompanied by elevated ERK activity in many human tumors. Studies have also shown that ERK is a critical component of Ras signalling. These observations support the attractiveness of the ERK1/2 signaling pathway for developing anticancer therapies in a broad spectrum of human tumors.

ERK inhibitors are known in the art; see, for example, WO2013130976. There remains a need to provide alternative ERK inhibitors, more particularly for the treatment of cancer. Accordingly, the present invention provides ERK1/2 inhibitors which may be useful for treating cancer.

The present invention provides a compound of the following formula:

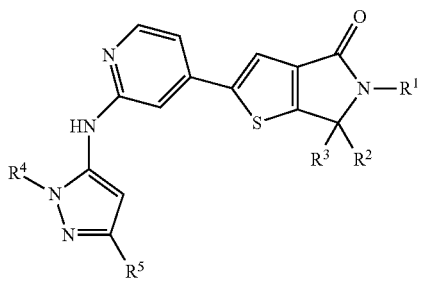

wherein:
$R^1$ is hydrogen, 2-methoxyethyl, 2-(cyclopropoxy)ethyl, 2-hydroxyethyl, 2-(2,2-difluoroethoxy)ethyl, 2-(trideuteriomethoxy)ethyl, 2-(trifluoromethoxy)ethyl, 2-methoxypropyl, (2R)-2-methoxypropyl, or (2S)-2-methoxypropyl;
$R^2$ and $R^3$ are independently hydrogen, methyl, or ethyl or $R^2$ and $R^3$ can be taken together to form cyclopropyl or cyclopentyl;
$R^4$ is hydrogen, methyl, ethyl, isopropyl, cyclopropyl, difluoromethyl, 2-fluoroethyl, 2,2-difluoroethyl, 2,2,2-trifluoroethyl, or 2-methoxyethyl; and
$R^5$ is hydrogen, methyl, or cyclopropyl;
or a pharmaceutically acceptable salt thereof.

The present invention provides an embodiment for a compound of Formula I wherein $R^1$ is 2-methoxyethyl.

The present invention also provides an embodiment for a compound of Formula I wherein $R^2$ and $R^3$ are independently methyl.

The present invention also provides another embodiment for a compound of Formula I wherein $R^4$ is methyl.

The present invention also provides yet a further embodiment for a compound of Formula I wherein $R^5$ is hydrogen.

Preferably, the present invention provides a compound which is 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one, or a pharmaceutically acceptable salt thereof.

As a particular embodiment, the present invention provides the compound which is 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one.

The present invention provides a pharmaceutical composition comprising 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one, or a pharmaceutically acceptable salt thereof, and a pharmaceutically acceptable carrier, diluent, or excipient. The present invention provides a pharmaceutical composition comprising 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one, and a pharmaceutically acceptable carrier, diluent, or excipient.

The present invention provides a method for treating cancer comprising administering to a patient in need thereof an effective amount 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one, or a pharmaceutically acceptable salt thereof. The present invention provides a method for treating cancer comprising administering to a patient in need thereof an effective amount 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one.

The present invention provides 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one, or a pharmaceutically acceptable salt thereof for use in therapy. The present invention provides 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one, or a pharmaceutically acceptable salt thereof, for use in the treatment of cancer. The present invention provides a pharmaceutical composition for use in treating cancer, the pharmaceutical composition comprising 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one, or a pharmaceutically acceptable salt thereof.

The present invention also provides 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one for use in therapy. The present invention provides 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one for use in the treatment of cancer. The present invention provides a pharmaceutical composition for use in treating cancer, the pharmaceutical composition comprising 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one.

The present invention provides the use of 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one, or a pharmaceutically acceptable salt thereof, in the manufacture of a medicament for the treatment of cancer. The present invention also provides the use of 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one in the manufacture of a medicament for the treatment of cancer.

The present invention provides 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one in a crystalline form. The present invention also provides 5-(2-methoxyethyl)-6,6-dimethyl-2-{2-[(1-methyl-1H-pyrazol- 5-yl)amino]pyridin-4-yl}-5,6-dihydro-4H-thieno[2,3-c]pyrrol-4-one in a crystalline form (Crystalline Form 1) characterized by a X-ray powder diffraction pattern having characteristic peaks, in 2θ±0.2°, occurring at 24.2° in combination with one or more of the peaks selected from the group consisting of 8.0°, 12.8°, 15.9°, 16.8°, and 19.5°. The present invention further provides 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one in a crystalline form (Crystalline Form 2) characterized by a X-ray powder diffraction pattern having characteristic peaks, in 2θ+0.2°, occurring at 18.5° in combination with one or more of the peaks selected from the group consisting of 8.5°, 9.2°, 16.5°, 20.3°, and 23.3°.

Furthermore, the present invention provides preferred embodiments of the methods and uses as described herein, in which cancer is selected from the group consisting of melanoma, colorectal cancer, pancreatic cancer, and non-small cell lung cancer. Preferred cancers are colorectal cancer, pancreatic cancer, and non-small cell lung cancer.

The present invention also provides 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one, or a pharmaceutically acceptable salt thereof, for use in simultaneous, separate or sequential administration in combination with one or more chemotherapy agents in the treatment of cancer.

The present invention preferably contains compounds of Formula I with the following substituents:
a) $R^1$ is 2-methoxyethyl;
b) $R^2$ is methyl;
c) $R^3$ is methyl;
d) $R^4$ is methyl; or
e) $R^5$ is hydrogen.

More preferably, the present invention contains compounds of Formula I with the following combinations of substituents:
a) $R^2$ and $R^3$ are methyl;
b) $R^1$ is 2-methoxyethyl, $R^2$ is methyl, and $R^3$ is methyl;
c) $R^1$ is 2-methoxyethyl, $R^4$ is methyl, and $R^5$ is hydrogen;
d) $R^2$ is methyl, $R^3$ is methyl, $R^4$ is methyl, and $R^5$ is hydrogen; or
e) $R^1$ is 2-methoxyethyl, $R^2$ is methyl, $R^3$ is methyl, $R^1$ is methyl, and $R^5$ is hydrogen.

As used above, and throughout the description of the invention, the following terms, unless otherwise indicated, shall be understood to have the following meanings:

A "pharmaceutically acceptable carrier, diluent, or excipient" is a medium generally accepted in the art for the delivery of biologically active agents to mammals, e.g., humans.

"Pharmaceutically acceptable salts" or "a pharmaceutically acceptable salt" refers to the relatively non-toxic, inorganic and organic salt or salts of the compound of the present invention.

"Effective amount" means the amount of the compound, or pharmaceutically acceptable salt thereof of the present invention or pharmaceutical composition containing a compound, or pharmaceutically acceptable salt thereof, of the present invention that will elicit the biological or medical response of or desired therapeutic effect on a tissue, system, animal, mammal or human that is being sought by the researcher, veterinarian, medical doctor or other clinician.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

It will be understood by the skilled artisan that compounds of the present invention are capable of forming salts. The compounds of the present invention contain basic heterocycles, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts", *Journal of Pharmaceutical Sciences*, Vol 66, No. 1, January 1977.

The compounds of the present invention are preferably formulated as pharmaceutical compositions administered by a variety of routes. Preferably, such compositions are for oral administration. Such pharmaceutical compositions and processes for preparing same are well known in the art. See. e.g., REMINGTON: THE SCIENCE AND PRACTICE OF PHARMACY (A. Gennaro, et al., 21$^{st}$ ed., Mack Publishing Co., 2005).

The compounds of the present invention are generally effective over a wide dosage range. For example, dosages per day normally fall within the daily range of about 1 to 2000 mg. Preferably such doses fall within the daily range of 50 to 1000 mg. More preferably such doses fall within the daily range of 125 to 400 mg. In some instances dosage levels below the lower limit of the aforesaid ranges may be more than adequate, while in other cases still larger doses may be employed, and therefore the above dosage ranges are not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The skilled artisan will appreciate that certain compounds of the present invention contain at least one chiral center. The present invention contemplates all individual enantiomers or diastereomers, as well as mixtures of the enantiomers and diastereomers of said compounds including racemates. It is preferred that compounds of the present invention containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques.

The designation of "isomer 1" in a compound name represents that the corresponding intermediate or compound of the present invention is the first of two eluting enantiomers when a mixture of a pair of enantiomers is separated by chiral chromatography. The designation of "isomer 2" in a compound name represents that the corresponding intermediate or compound of the present invention that is the second of two eluting enantiomers when the mixture of a pair of enantiomers is separated by chiral chromatography.

The compounds of the present invention can be prepared according to synthetic methods well known and appreciated in the art. Suitable reaction conditions for the steps of these reactions are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

As used herein, the following terms have the meanings indicated: "ACN" refers to acetonitrile; "DCM" refers to dichloromethane; "DMF" represents N,N-dimethylformamide; "DMSO" refers to dimethyl sulfoxide; "DTT" refers to dithiothreitol; "EDTA" refers to ethylenediaminetetraacetic acid; "EGTA" refers to ethylene glycol tetraacetic acid; "ELISA" refers to enzyme-linked immunosorbent assay; "EtOAc" refers to ethyl acetate; "EtOH" refers to ethanol; "FBS" refers to fetal bovine serum; "HBSS" refers to Hank's Balanced Salt Solution; "IC$_{50}$" refers to half maximal inhibitory concentration; "IVTI" refers to in vivo target inhibition; "MS" refers to mass spectroscopy; "MeOH" refers to methanol; "NMR" refers to nuclear magnetic resonance; "PBST" refers to phosphate buffered saline containing Tween-20; "TED50" refers to Threshold Effective Dose 50; "THF" refers to tetrahydrofuran; "UVW" refers to ultra-violet wavelength, and "XRD" refers to X-ray diffraction.

Unless noted to the contrary, the compounds illustrated herein are named and numbered using either ACDLABS or Accelrys Draw 4.1.

Compounds of the present invention may be synthesized as illustrated in the following schemes, where $R^1$, $R^2$, $R^3$, $R^4$, and $R^5$ are as previously defined.

Scheme 1: Synthesis of compounds of Formula I

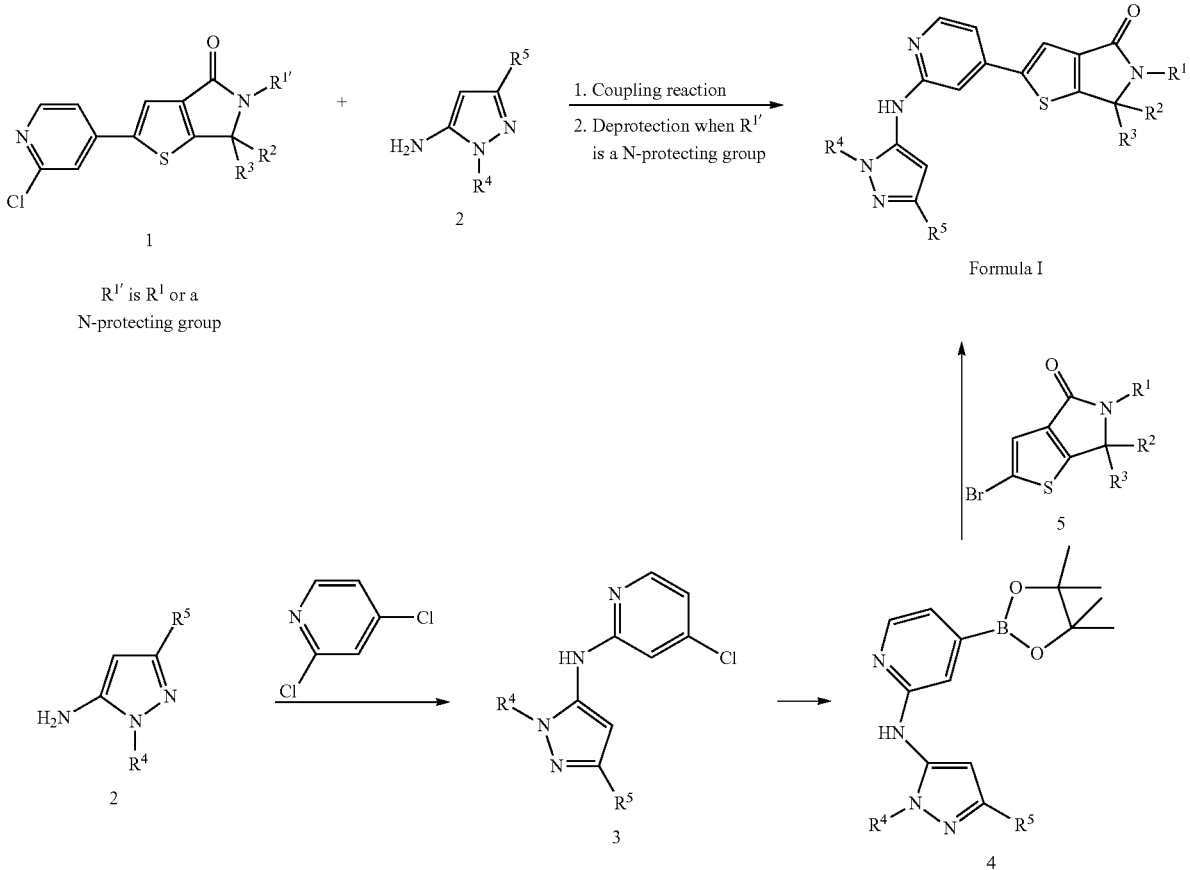

Scheme 1 illustrates the synthetic method to make compounds of Formula I. Compound 1 is reacted with Compound 2 under well-known palladium coupling reaction conditions to provide compounds of Formula I. More specifically, a compound of Formula I is obtained by reacting Compound 1 and Compound 2 under an elevated temperature in a suitable solvent such as 1,4-dioxane or toluene, with the existence of a suitable base such as cesium carbonate or tert-butoxide, a suitable catalyst such as palladium(II)acetate or bis(tri-o-tolylphosphine)palladium(0), and a suitable ligand agent such as 4,5-bis(diphenylphosphino)-9,9-dimethylxanthene or (R)-1-[(Sp)-2-(dicyclohexylphosphino)ferrocenyl]ethyldi-tert-butylphosphine. When $R^{1'}$ is an N-protecting group, the coupling product is further treated with a suitable de-protecting agent such as trifluoroacetic acid in a suitable solvent such as DCM to provide a compound of Formula I when $R^1$ is hydrogen.

Compound of Formula I can be synthesized with an alternative method as illustrated in Scheme 1. Compound 2 is reacted with 2,4-dichloropyridine under well-known palladium coupling reaction conditions to provide Compound 3. More specifically, Compound 3 is obtained by reacting Compound 2 and 2,4-dichloropyridine at an elevated temperature in a suitable solvent such as 1,4-dioxane, in the presence of a suitable catalyst such as tris(dibenzylideneacetone)dipalladium(0) and a suitable base such as cesium carbonate. Compound 3 is reacted with bis(pinacolato)diboron under well-known palladium coupling reaction conditions to provide Compound 4. More specifically, Compound 3, bis(pinacolato)diboron, a suitable ligand agent such as 2-dicyclohexylphosphino-2',4',6'-triisopropylbiphenyl and a suitable catalyst such as chloro(2-dicyclohexylphosphino-2',4',6'-triisopropyl-1,1'-biphenyl)[2-(2'-amino-1,1'-biphenyl)]palladium(II) are heated at an elevated temperature in a suitable solvent such as absolute EtOH to provide Compound 4. Compound 4 is reacted with Compound 5 under well-known palladium coupling reaction conditions to provide a compound of Formula I.

Scheme 2: Synthesis of Compound 1

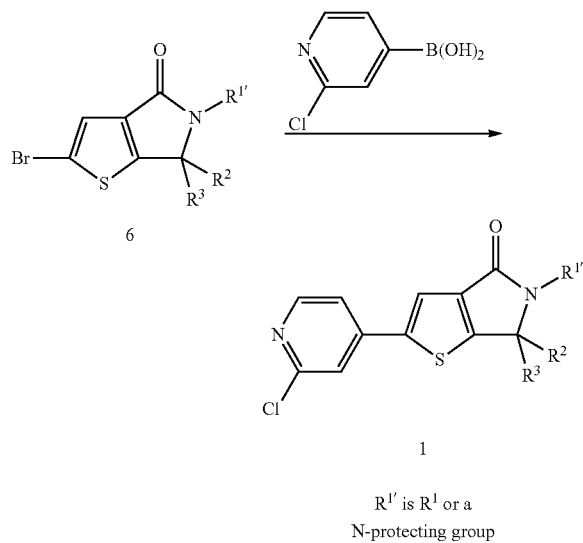

R¹' is R¹ or a
N-protecting group

Scheme 2 illustrates the synthetic method of Compound 1. Compound 6 is reacted with 2-chloropyridine-4-boronic acid under well-known palladium coupling reaction conditions to provide Compound 1. More specifically, Compound 6 is reacted at elevated temperature with 1,2-chloropyridine-4-boronic acid, a suitable base such as sodium carbonate, a suitable catalyst such as trans-dichloro-bis-triphenylphosphine palladium (II) in a suitable solvent such as a mixture of EtOH and water to provide Compound 1.

Scheme 3: Alternative synthesis of Compound 1 when R¹' is R¹

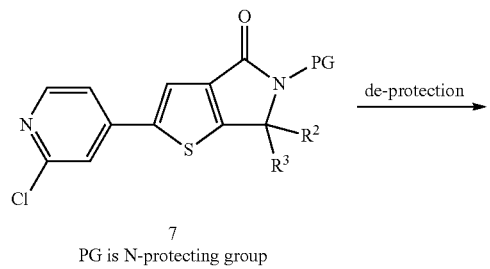

PG is N-protecting group

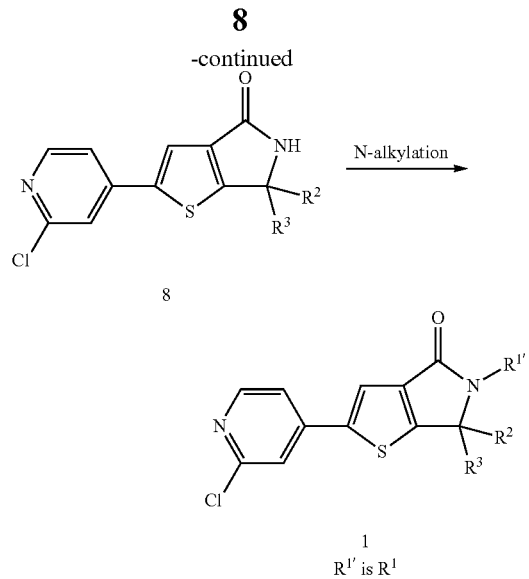

Scheme 3 illustrates an alternative synthetic method of Compound 1 when R¹' is R¹. Compound 7, which can be made by the synthetic method as illustrated in Scheme 2 when R¹' is a suitable N-protecting group, is reacted with a suitable de-protecting agent such as trifluoroacetic acid in a suitable solvent such as DCM to provide Compound 8. Compound 8 is further reacted with a suitably substituted alkylation agent to provide Compound 1 when R¹' is R¹ as previously defined. More specifically, Compound 7 is treated with a suitable base such as sodium hydride and then followed by the reaction with an suitably substituted alkylation agent such as methyl iodide or iodoethoxycyclopropane in a suitable solvent such as DMF to provide Compound 1 when R¹' is R¹ as previously defined.

Scheme 4: Synthesis of Compound 2

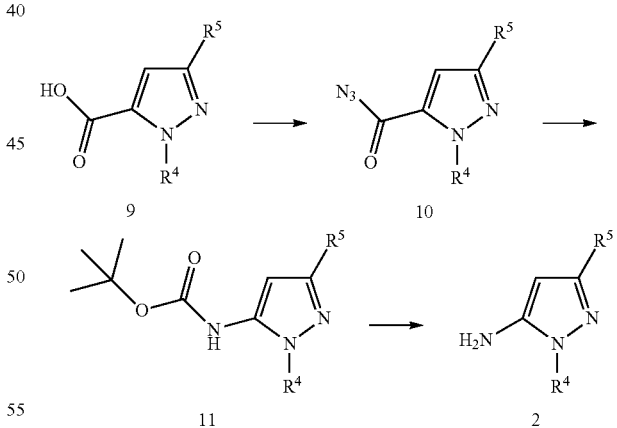

Compound 2 is either commercially available or made by the synthetic method as illustrated in Scheme 4. Compound 9 is treated with diphenylphosphoryl azide and a suitable base such as triethylamine in a suitable solvent such as a mixture of THF and DCM to provide Compound 10. Compound 10 is then reacted with tert-butyl alcohol under elevated temperature to provide Compound 11. Compound 11 is treated with a suitable de-protecting agent such as hydrogen chloride in a suitable solvent such as DCM to provide Compound 2.

Scheme 5: Synthesis of Compound 6

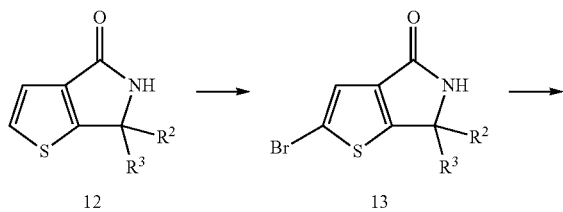

Scheme 5 illustrates the synthetic method for Compound 6. Compound 12 is reacted with a suitable bromination agent such as N-bromosuccinimide in a suitable solvent such as ACN to provide Compound 13. Compound 13 is reacted with a suitable base such as N,N-dimethylpyridin-4-amine, N,N-diisopropylethylamine, sodium hydride or sodium hexamethyldisilylazide, and a suitable N-alkylation or N-protecting agent such as 2-methoxyethyl bromide, 2-chloroethoxycyclopropane, or di-tert-butyldicarbonate to provide Compound 6.

Preparation 1

2-Methoxypropyl 4-methylbenzenesulfonate

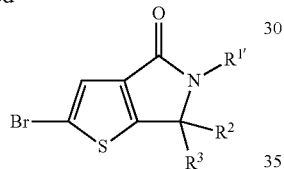

Cool a solution of 2-methoxypropan-1-ol (1.0 g, 11.1 mmol) in pyridine (12.5 mL) and DCM (19 mL) in an ice water bath and add 4-methylbenzenesulfonyl chloride (2.54 g, 13.3 mmol). Stir the mixture overnight while allowing the temperature to rise slowly to ambient temperature. Quench the reaction with water (40 mL) and EtOAc (50 mL). Separate the phases and extract the aqueous phase twice with additional EtOAc (50 mL). Wash the combined organic solutions with saturated aqueous ammonium chloride and saturated NaCl. Dry the organics over anhydrous magnesium sulfate. Filter and concentrate the filtrate to give the title compound 2.71 g (91%) as a colorless oil. MS (m/z): 245 (M+1).

The following compound is prepared essentially by the method of Preparation 1.

TABLE 1

Preparation 2

| Prep. No. | Compound Name | Structure | MS (m/z): |
|---|---|---|---|
| 2 | 2-(Trideuteriomethoxy)ethyl 4-methylbenzenesulfonate) | 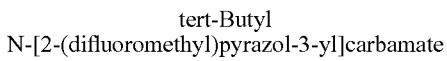 | 234 (M + 1) |

-continued

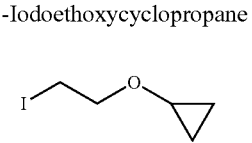

6
R[1'] is R[1] or a N-protecting group

Preparation 3

2-Iodoethoxycyclopropane

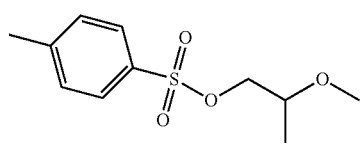

In a microwave reactor, heat a solution of 2-chloroethoxycyclopropane (750 mg, 6.2 mmol) and sodium iodide (2.8 g, 18.7 mmol) in acetone (62 mL) at 75° C. for 18 hours. Dilute the reaction mixture with a 1:1 mixture of hexanes and pentane. Filter the mixture through a CELITE® plug and wash the solids with ether. Concentrate the filtrate under reduced pressure at room temperature. Dilute the product with ether (5 mL) and sonicate the mixture in a water bath. Filter the resulting suspension through an additional CELITE® plug and wash the solids with ether. Concentrate the filtrate to a minimum volume (3.5 mL) and add magnesium sulfate. Use this solution in the next step. $^1$H NMR (399.83 MHz, DMSO-$d_6$) δ 3.65 (t, J=6.3 Hz, 2H), 3.35-3.30 (m, 1H), 3.30 (t, J=6.3 Hz, 2H), 0.49-0.45 (m, 2H), 0.43-0.38 (m, 2H).

Preparation 4 tert-Butyl N-[2-(difluoromethyl)pyrazol-3-yl]carbamate

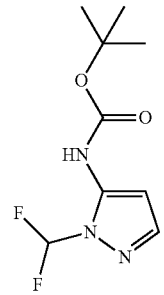 [SMILES: CC(C)(C)OC(=O)Nc1ccnn1C(F)F]

Cool a solution of 2-(difluoromethyl)pyrazole-3-carboxylic acid (2.0 g, 12.3 mmol) in THF (16.5 mL) and DCM (19 mL) in an ice water bath and add triethylamine (2.6 mL, 18.5 mmol) and diphenylphosphoryl azide (4.0 mL, 18.5 mmol). Stir the reaction overnight while allowing the reaction temperature to rise slowly. Add tert-butyl alcohol (2.3 mL, 24.7 mmol) and heat the reaction mixture at 70° C. for two hours. Remove the heat and stir the reaction mixture for two days. Heat the reaction mixture at 70° C. for an additional 18 hours and then cool to room temperature. Concentrate the mixture under reduced pressure and purify the residue by silica gel column chromatography (220 g column) eluting with a gradient from 0-100% EtOAc in hexanes. Combine fractions containing the desired product and concentrate under reduced pressure. Purify the resulting residue by reverse phase chromatography (15 g C-18 Reverse Phase Gold column; 0% held for 5 min, 0-20% ACN/water elution gradient). Further purify the material obtained by silica gel column (220 g) chromatography eluting with a gradient from 0-30% EtOAc in DCM to give the title compound 1.28 g (44%). MS (m/z): 234 (M+1).

The following compounds are prepared essentially by the method of Preparation 4.

Preparation 7

2-(Difluoromethyl)pyrazol-3-amine hydrochloride

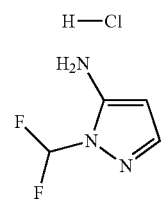

Treat a solution of tert-butyl N-[2-(difluoromethyl)pyrazol-3-yl]carbamate (1.28 g, 5.5 mmol) in DCM (11 mL) with hydrogen chloride (4.0 M in 1,4-dioxane, 5.5 mL, 22 mmol). Stir the mixture at room temperature for two days. Concentrate the mixture under reduced pressure to give the title compound 920 mg (99%) as a white solid. $^1$H NMR (399.83 MHz, DMSO-$d_6$) δ 7.5-8.77 (br S, 3H), 7.58 (t, J=55.6 Hz, 1H), 7.33 (s, 1H), 5.31 (s, 1H).

The following compounds are prepared essentially by the method of Preparation 7.

TABLE 2

| Preparations 5-6 | | | |
|---|---|---|---|
| Prep. No. | Compound Name | Structure | Physical Data |
| 5 | tert-Butyl N-[2-(2-fluoroethyl)pyrazol-3-yl]carbamate | | $^1$H NMR (400.15 MHz, DMSO-$d_6$) δ 9.24 (br, 1H), 7.32 (d, J = 2.0 Hz, 1H), 6.07 (s, 1H), 4.72 (t, J = 4.8 Hz, 1H), 4.60 (t, J = 4.8 Hz, 1H.), 4.30 (t, J = 4.8 Hz, 1H), 4.23 (t, J = 4.8 Hz, 1H), 1.42 (s, 9H). |
| 6 | tert-Butyl N-(2-cyclopropylpyrazol-3-yl)carbamate | | 224 (M + 1) |

TABLE 3

Preparations 8-9

| Prep. No. | Compound Name | Structure | Physical Data | Comment |
|---|---|---|---|---|
| 8 | 2-(2-Fluoroethyl)pyrazol-3-amine | (structure) | $^1$H NMR (399.83 MHz, DMSO-$d_6$) δ 7.03 (d, J = 1.6 Hz, 1H), 5.23 (d, J = 1.7 Hz, 1H), 5.12 (bs, 2H), 4.70 (t, J = 5.1 Hz, 1H), 4.58 (t, J = 5.1 Hz, 1H) 4.16 (t, J = 5.1 Hz, 1H), 4.10 (t, J = 5.1 Hz, 1H), | Free base is made with sodium bicarbonate |
| 9 | 2-Cyclopropylpyrazol-3-amine hydrochloride | (structure) | $^1$H NMR (399.83 MHz, DMSO-$d_6$) δ 7.80 (S, 1H), 6.28-7.58 (br S, 1H), 5.62 (s, 1H), 3.23-3.28 (m, J = 3.6 Hz, 1H), 1.024-1.11 (m, J = 3.6 Hz, 4H). | |

Preparation 10

6,6-Dimethylthieno[2,3-c]furan-4-one

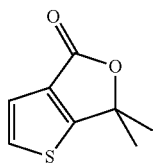

Cool a solution of 3-thiophenecarboxylic acid (250 g, 1.95 mol) in THF (9750 mL) to −70° C. in a 20 L 3-neck flask. To this solution, add n-butyl lithium (2.5 M in hexane, 1872 mL, 4.68 mol) slowly while maintaining the temperature below −55° C. Stir the reaction mixture for one hour at −70° C. Add acetone (187 mL, 2.55 mol) slowly at −70° C. Allow the reaction mixture to warm to 0° C. and stir for three hours at 0° C. To the resulting solution, add 4 M hydrochloric acid (1500 mL) at 0° C. and allow the reaction mixture to warm to room temperature. Stir the resulting mixture overnight. Filter the reaction mixture through a diatomaceous earth pad and wash the pad with toluene (3×500 mL). Concentrate the filtrate under reduced pressure. Dissolve the resulting crude residue in toluene (3750 mL) and water (250 mL) and add p-toluene sulfonic acid (100.1 g, 0.526 mol) at room temperature. Reflux the reaction mixture for 16 hours at 100° C. Cool the reaction to room temperature and concentrate under reduced pressure at 50° C. Dissolve the resulting residue in water and extract with EtOAc (2×10 L). Wash the organic layer with saturated aqueous sodium bicarbonate and water. Dry the combined organic extracts over anhydrous sodium sulfate, filter and concentrate under reduced pressure at 50° C. to provide the title compound 200 g (61%) as brown viscous liquid. MS (m/z): 169 (M+1).

Preparation 11

6,6-Dimethyl-5H-thieno[2,3-c]pyrrol-4-one

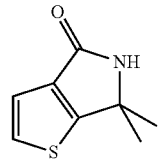

Charge a 5 L autoclave with a solution of 6,6-dimethyl-thieno[2,3-c]furan-4-one (150 g, 0.891 mol) in ammonium hydroxide (1000 ml). In a closed environment, bring the reaction mixture carefully to a temperature of 200° C. and stir for four hours at 200° C. After four hours, cool the reaction mixture to room temperature and release the ammonia gas. Extract the reaction mixture with DCM (3×750 mL). Wash the organic layer with water (1×750 mL), and dry over anhydrous sodium sulfate, filter and concentrate the filtrate under reduced pressure at 50° C. to provide the title compound 100 g (67%). MS (m/z): 168 (M+1).

Preparation 12

Methyl 2-bromothiophene-3-carboxylate

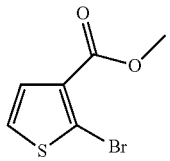

Treat a solution of 2-bromothiophene-3-carboxylic acid (65 g, 314 mmol) in MeOH (500 mL) with thionyl chloride (13.5 g, 113 mmol) at room temperature. Stir the mixture for 30 minutes at room temperature and then heat the mixture to reflux for three hours. Allow the mixture to cool while stirring overnight. Concentrate the reaction mixture under reduced pressure. Add EtOAc and wash the resulting organic solution with saturated aqueous sodium bicarbonate. Separate the layers and back extract the aqueous solution with additional EtOAc. Combine the organic solutions and dry over anhydrous sodium sulfate. Filter the solution and concentrate the filtrate under reduced pressure. Purify the residue by silica gel column chromatography by loading the product onto a 220 g pre-column and eluting the pre-column onto a 330 g column with a gradient from 10-25% EtOAc in DCM. Combine the appropriate fractions and concentrate under reduce pressure to give the title compound 71 g. Use the material without further purification. $^1$H NMR (400.15 MHz, DMSO-$d_6$) δ 7.36-7.34 (d, J=5.6 Hz, 1H), 7.22-7.20 (d, J=5.6 Hz, 1H), 3.87 (s, 3H).

Preparation 13

Methyl 2-acetylthiophene-3-carboxylate

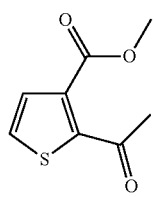

Purge a solution of methyl 2-bromothiophene-3-carboxylate (58.5 g, 265 mmol) and (1-ethoxyethenyl)trimethylstannane (106 g, 294 mmol) in 1,4-dioxane (350 mL) with nitrogen for five minutes. Add bis(triphenylphosphine)palladium(II) chloride (3.71 g, 5.29 mmol) all a once and heat the reaction at 95° C. for 24 hours. Cool the reaction to room temperature and treat the reaction with 1 N hydrochloric acid (100 mL). Stir the mixture vigorously for 30 minutes. Reduce the reaction volume by 50% under reduced pressure. Dilute the mixture with EtOAc (500 mL) and filter the resulting solution through CELITE®. Wash the solid with additional EtOAc and transfer the filtrate to a separatory funnel. Wash the organic solution with saturated NaCl. Back extract the aqueous solution with additional EtOAc. Combine the organic solutions and concentrate under reduced pressure. Purify the residue by silica gel column chromatography by loading the product onto a 220 g pre-column and eluting the pre-column onto a 330 g column with a gradient from 10-25% EtOAc in hexanes to give the title compound 42.7 g (88%). MS (m/z): 185 (M+1).

Preparation 14

Methyl 2-[1-(2-methoxyethylamino)ethyl]thiophene-3-carboxylate

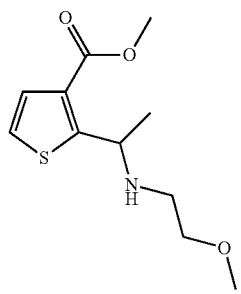 [SMILES: COCCNC(C)c1sccc1C(=O)OC]

Treat a solution of methyl 2-acetylthiophene-3-carboxylate (42.7 g, 232 mmol) in MeOH (45 mL) with 2-methoxyethylamine (35 g, 466 mmol) drop wise using a water bath to keep the temperature from rising. Allow the mixture to stand at room temperature overnight. Treat the mixture with 5% palladium on carbon (28 g) and subject the mixture to a hydrogen atmosphere (50 PSI) at 50° C. for 18 hours. Cool the mixture to room temperature and vent the gas. Filter the mixture and wash the solid with MeOH. Concentrate the mixture to give the title compound 47 g (83%) as an amber oil. MS (m/z): 244 (M+1).

Preparation 15

5-(2-Methoxyethyl)-6-methyl-6H-thieno[2,3-c]pyrrol-4-one

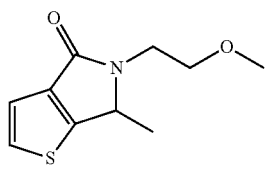

Treat a solution of methyl 2-[1-(2-methoxyethylamino)ethyl]thiophene-3-carboxylate (9.4 g, 39 mmol) in THF (50 mL) with bis(trimethylaluminum)-1,4-diazabicyclo[2.2.2]octane adduct (0.1 g, 0.4 mmol) and heat the resulting mixture at 60° C. overnight. Cool the reaction to room temperature. Carefully quench the reaction mixture drop wise with saturated aqueous ammonium chloride followed by 1 N hydrochloric acid. Add EtOAc and extract. Separate the layers and treat the aqueous layer with additional 1 N hydrochloric acid until the solution is clear. Extract the aqueous solution with four portions EtOAc. Combine the organic extracts and dry the solution over anhydrous sodium sulfate. Filter the mixture and concentrate the filtrate to give the title compound 8 g (98%) as an amber oil. MS (m/z): 212 (M+1).

Preparation 16

Spiro[5H-thieno[2,3-c]pyrrole-6,1'-cyclopropane]-4-one

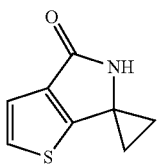 [SMILES: O=C1NC2(CC2)c2sccc21]

Treat a −70° C. solution of methyl 2-cyanothiophene-3-carboxylate (3 g, 17.4 mmol) and titanium tetra(isopropoxide) (5.44 g, 19.2 mmol) in diethyl ether (145 mL) with a solution of ethylmagnesium bromide in diethyl ether (12.8 mL, 38.3 mmol). Stir the reaction mixture for 30 minutes. Remove the cooling bath and allow the mixture to slowly warm to room temperature over one hour. Add boron trifluoride etherate (4.4 mL, 34.8 mmol) and stir the mixture for an additional one hour. Quench the reaction with 1 N hydrochloric acid (87 mL). Dilute the reaction with diethyl ether (200 mL). Separate the layers and back extract the aqueous layer with additional diethyl ether. Combine the organic extracts and wash with saturated aqueous sodium bicarbonate and saturated NaCl. Dry the organic solution over sodium sulfate, filter and concentrate the filtrate under reduced pressure. Purify the residue by silica gel column chromatography by loading the product onto a 25 g pre-column and eluting the pre-column onto a 80 g column with EtOAc to give the title compound 1.02 g (35%). MS (m/z): 166 (M+1).

Preparation 17

5-Bromo-2-methyl-thiophene-3-carboxylic acid

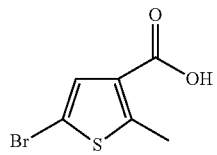

Cool a solution of 2-methylthiophene-3-carboxylic acid (50 g, 352 mmol) in acetic acid (75 mL) and DMF (300 mL) in an ice water bath and add N-bromosuccinimide (69 g, 387 mmol). After the addition, remove the ice bath and stir the reaction mixture for two hours. Pour the reaction onto ice chips and add EtOAc. Separate the layers and wash the organic layer with two portions water, one portion saturated aqueous sodium bicarbonate and saturated NaCl. Extract the original aqueous solution with three portions EtOAc. Combine all EtOAc extracts and dry over sodium sulfate. Filter the solution and wash the solid with additional EtOAc. Concentrate the filtrate to a solid. Add water and shake the flask to disperse the solid. Filter the solids and wash the solids with water. Collect the solid and dry in a vacuum oven. Extract the filtrate with three portions EtOAc, combine the extracts, and concentrate to a solid. Combine all solids to give the title compound 46 g (59%). MS (m/z): 221/223 (M+1/M+3).

Preparation 18

5-Bromo-2-(dibromomethyl)thiophene-3-carboxylic acid

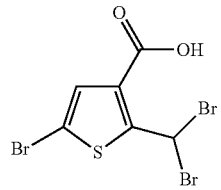 [SMILES: O=C(O)c1cc(Br)sc1C(Br)Br]

Treat a solution of 5-bromo-2-methyl-thiophene-3-carboxylic acid (46 g, 208 mmol) in carbon tetrachloride (500 mL) with N-bromosuccinimide (93 g, 520 mmol) and benzoyl peroxide (2.5 g, 10.4 mmol). Heat the reaction mixture at 80° C. overnight. Cool the mixture to room temperature and concentrate to dryness under reduced pressure. Add water and shake the mixture to break up the solids. Filter the mixture and wash the solids with water (1 L). Air dry the resulting solid to give the title compound 66 g (84%). $^1$H NMR (400.15 MHz, DMSO-$d_6$) δ 7.83 (s, 1H), 7.40 (s, 1H).

Preparation 19

5-Bromo-2-formyl-thiophene-3-carboxylic acid

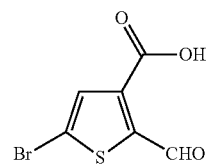

Treat a solution of 5-bromo-2-(dibromomethyl)thiophene-3-carboxylic acid (66 g, 150 mmol) in 1,4-dioxane (594 mL) and water (132 mL) with sulfuric acid (12.6 mL) and stir the mixture at 80° C. overnight. Concentrate the reaction to a residue. Add water and shake the mixture to form a precipitate. Collect the solid by vacuum filtration in a sintered glass funnel and wash the solids with water until wash pH is over 4. Dry the solid to give the title compound 36 g. The compound is used without further purification. MS (m/z): 235/237 (M+1/M+3).

Preparation 20

Methyl 5-bromo-2-[[tert-butoxycarbonyl(2-methoxyethyl)amino]methyl]thiophene-3-carboxylate

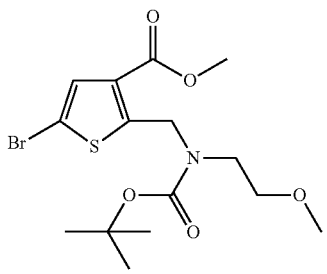 [SMILES: COCCN(Cc1sc(Br)cc1C(=O)OC)C(=O)OC(C)(C)C]

Treat a solution of 5-bromo-2-formyl-thiophene-3-carboxylic acid (9 g, 38 mmol) in MeOH (300 mL) with 2-methoxyethylamine (5.01 mL, 57 mol) and stir the mixture at room temperature overnight. Treat the reaction with sodium cyanoborohydride (7.2 g, 115 mmol) and stir the mixture for two hours. Add additional sodium cyanoborohydride (2 g, 32 mmol) and stir the mixture for an additional hour. Concentrate the reaction mixture to dryness and co-evaporate with one portion DCM. Dissolve the residue in 1,4-dioxane (280 mL) and water (75 mL) and treat the resulting solution with potassium carbonate (11.5 g) and di-tert-butyldicarbonate (16.7 g). Stir the mixture at room temperature overnight. Dilute the reaction with water and saturated NaCl. Extract with three portions EtOAc. Combine the organic extracts and dry over anhydrous sodium sulfate. Purify the residue by silica gel column chromatography by loading the product onto a 260 g pre-column and eluting the pre-column onto a 330 g column with a gradient from 0-100% EtOAc in DCM and then a second gradient from 100% EtOAc to 7% MeOH in DCM to give the title compound 2.76 g (18%). MS (m/z): 408/410 (M+1/M+3).

Preparation 21

Methyl 5-bromo-2-[(2-methoxyethylamino)methyl]thiophene-3-carboxylate

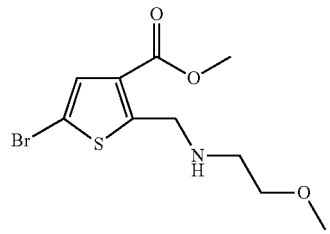 [SMILES: COCCNCc1sc(Br)cc1C(=O)OC]

Treat 5-bromo-2-[[tert-butoxycarbonyl(2-methoxyethyl)amino]methyl]thiophene-3-carboxylate, (2.75 g, 6.7 mmol) with hydrogen chloride (4 M in 1,4-dioxane, 30 mL, 120 mmol) and stir the mixture for 45 minutes. Concentrate the mixture to dryness. Dissolve the residue in ACN and treat the mixture with potassium carbonate (1.5 g). Heat the mixture at reflux for four hours. Concentrate the mixture to dryness and add DCM. Filter the suspension and concentrate the filtrate to give the title compound 2.05 g (99%) as a dark oil. MS (m/z): 308/310 (M+1/M+3).

Preparation 22

5-Bromo-2-[(2-methoxyethylamino)methyl]thiophene-3-carboxylic acid

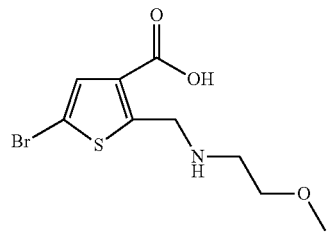

Treat a solution of methyl 5-bromo-2-[(2-methoxyethylamino)methyl]thiophene-3-carboxylate, (2.05 g, 6.7 mmol) in THF (75 mL) and water (25 mL) with lithium hydroxide (558 mg, 13 mmol) and stir the mixture overnight. Concentrate the mixture to near dryness and treat the residue with hydrochloric acid (4 M in 1,4-dioxane, 7 mL). Stir the mixture for one minute and concentrate to dryness. Dissolve the residue in 5% MeOH in DCM and dry the resulting mixture with magnesium sulfate. Filter the mixture and concentrate the filtrate. Dry the material in a vacuum oven at 50° C. overnight to give the title compound 1.96 g (100%). MS (m/z): 294/296 (M+1/M+3).

Preparation 23

2-Bromo-5-(2-methoxyethyl)-6H-thieno[2,3-c]pyrrol-4-one

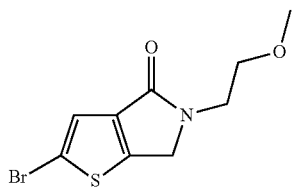

Treat a solution of 5-bromo-2-[(2-methoxyethylamino)methyl]thiophene-3-carboxylic acid, (1.96 g, 6.7 mmol) in DCM (10 mL) and N,N-diisopropylethylamine (10 mL) with DMF (5 mL). Treat the resulting solution with O-(7-azabenzotriazol-1-yl)-N,N,N',N'-tetramethyluronium hexafluorophosphate (5.1 g, 13.3 mmol) and stir the mixture for one hour. Dilute the reaction with DCM and water and separate the layers. Extract the aqueous solution with two portions DCM. Combine the organic extracts and wash with water and saturated NaCl, dry over magnesium sulfate, filter and concentrate the filtrate under reduced pressure. Purify the residue by silica gel column chromatography by loading the product onto a 25 g pre-column and eluting the pre-column onto a 120 g column with a gradient from 20-80% EtOAc in hexanes to give the title compound 0.920 g (50%). MS (m/z): 276/278 (M+1/M+3).

Preparation 24

Methyl 2-(cyclopenten-1-yl)thiophene-3-carboxylate

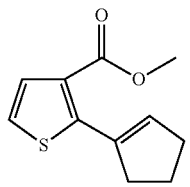

Treat a solution of 3-thiophenecarboxylic acid (20 g, 156 mmol) in THF (500 mL) at −75° C. with n-butyl lithium (2.5 M in hexane, 150 mL, 375 mmol) dropwise and stir the reaction mixture for one hour at −75° C. Add cyclopentanone (17 mL, 93 mmol) dropwise over 10 minutes and remove the cooling bath and allow the mixture to warm to room temperature over two hours. Cool the mixture to 0° C.

and slowly add hydrochloric acid (4 M in 1,4-dioxane, 120 mL, 480 mmol) over 30 minutes. Wash the mixture with water and saturated NaCl. Dry the organic solution over anhydrous sodium sulfate, filter and concentrate the filtrate under reduced pressure. Dissolve the residue in MeOH (300 mL) and add hydrochloric acid (4 M in 1,4-dioxane, 30 mL, 468 mmol). Heat the resulting mixture to reflux for two days. Cool the reaction mixture to room temperature and concentrate under reduced pressure. Dilute the residue with DCM (200 mL) and wash with saturated aqueous sodium bicarbonate (300 mL). Back extract the aqueous layer with DCM (2×150 mL) and combine the organics. Dry the combined organics over sodium sulfate, filter and concentrate under reduced pressure. Purify the residue by loading the material onto a plug of silica gel with DCM and eluting the plug with 25% EtOAc in hexanes to give the title compound 15 g (67%). MS (m/z): 209 (M+1). $^1$H NMR (399.80 MHz, DMSO-$d_6$) δ 7.41-7.42 (d, J=5.2 Hz, 1H), 7.30-7.31 (d, J=5.2 Hz, 1H), 6.17-6.21 (q, J=2 Hz, 1H), 3.74 (s, 3H), 2.58-2.71 (m, J=5.2 Hz, 2H), 2.50-2.93 (m, J=5.2 Hz, 2H), 1.87-1.98 (m, 2H).

Preparation 25

2-Bromospiro[5H-thieno[2,3-c]pyrrole-6,1'-cyclopentane]-4-one

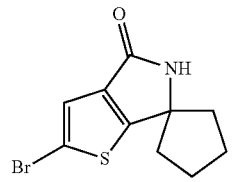 [SMILES: O=C1NC2(CCCC2)c2sc(Br)cc21]

In a PARR® autoclave, heat a solution of methyl 2-(cyclopenten-1-yl)thiophene-3-carboxylate (12 g, 58 mmol) in ammonia (7 N in MeOH, 250 mL) at 200° C. for three days. Cool the reaction to room temperature and dilute with saturated aqueous sodium bicarbonate (200 mL). Extract the mixture with EtOAc (2×250 mL). Combine the organic extracts and dry over sodium sulfate, filter, and concentrate the filtrate under reduced pressure. Treat the residue with ACN (250 mL) and N-bromosuccinimide (4.4 g, 25 mmol) and stir the mixture at room temperature for five hours. Dilute the reaction mixture with EtOAc (400 mL) and wash the organic mixture with saturated aqueous sodium bicarbonate (300 mL), water (3×300 mL), and saturated NaCl (200 mL). Dry the organic solution over anhydrous sodium sulfate, filter and concentrate the filtrate under reduced pressure. Purify the residue by silica gel column (330 g) chromatography eluting with a gradient from hexanes to EtOAc. Combine the fractions containing product and concentrate under reduced pressure. Purify the residue again by silica gel column (330 g) chromatography eluting with a gradient from hexanes to EtOAc to give the title compound 3.6 g (23%). MS (m/z): 272/274 (M+1/M+3).

Preparation 26

2-Bromo-6,6-dimethyl-5H-thieno[2,3-c]pyrrol-4-one

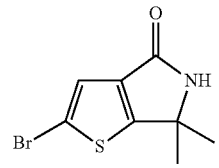

To a 20 L flask containing 6,6-dimethyl-5H-thieno[2,3-c]pyrrol-4-one (835 g, 4.99 mol) add ACN (10 L) and cool the solution to 10° C. Add N-bromosuccinimide (444.4 g, 2.49 mol) in four equal portions to the reaction mixture and stir for six hours at 25° C. Concentrate the reaction mixture under reduced pressure and slurry the resulting compound in water and extract with EtOAc (3×4.1 L). Wash the combined organic layer with water (3×4.1 L) and saturated NaCl (4.1 L), dry over anhydrous sodium sulfate, and filter. Store the organic solution for combination with additional batches.

Using the same process as above, prepare two additional batches starting with 650 g and 835 g 6,6-dimethyl-5H-thieno[2,3-c]pyrrol-4-one respectively. Combine the organic solutions from all three runs and concentrate under reduced pressure at 50° C. to yield 2-bromo-6,6-dimethyl-5H-thieno[2,3-c]pyrrol-4-one as brown sticky material. Slurry the resulting product in diethyl ether/hexane (2:1 v/v) and filter to provide the title compound 1542 g (45%). MS (m/z): 246/248 (M+1/M+3).

The following compounds are prepared essentially by the method of Preparation 26.

TABLE 4

Preparations 27-28

| Prep. No. | Compound Name | Structure | MS (m/z): |
|---|---|---|---|
| 27 | 2-Bromo-5-(2-methoxyethyl)-6-methyl-6H-thieno[2,3-c]pyrrol-4-one | 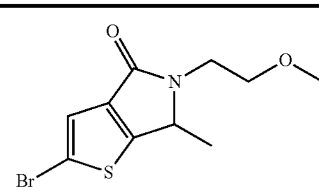 | 290/292 (M + 1/M + 3) |

TABLE 4-continued

Preparations 27-28

| Prep. No. | Compound Name | Structure | MS (m/z): |
|---|---|---|---|
| 28 | 2-Bromospiro[5H-thieno[2,3-c]pyrrole-6,1'-cyclopropane]-4-one | 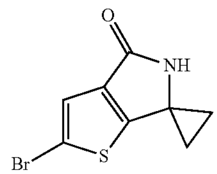 [SMILES: O=C1NC2(CC2)c2sc(Br)cc21] | 244/246 (M + 1/M + 3) |

Preparation 29

2-Bromo-6-ethyl-5-(2-methoxyethyl)-6-methyl-thieno[2,3-c]pyrrol-4-one

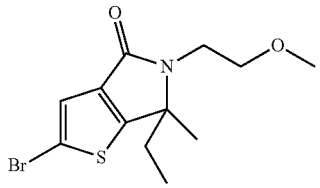 [SMILES: CCC1(C)c2sc(Br)cc2C(=O)N1CCOC]

Treat a solution of 2-bromo-5-(2-methoxyethyl)-6-methyl-6H-thieno[2,3-c]pyrrol-4-one (1.0 g, 3.4 mmol) in THF (20 mL) with sodium hydride (60% in mineral oil, 450 mg, 11 mmol). Stir the reaction mixture at room temperature overnight. Add iodoethane (1.4 mL, 17 mmol) dropwise and stir the mixture for an additional 24 hours. Cool the reaction in an ice water bath and quench with MeOH. Add EtOAc and wash the resulting organic solution with saturated NaCl. Back extract the aqueous layer with additional EtOAc. Combine the organic extracts and dry over anhydrous sodium sulfate. Filter and concentrate the filtrate under reduced pressure. Purify the residue by silica gel column chromatography by loading the product onto a 40 g pre-column and eluting the pre-column onto a 320 g column with 20% EtOAc in DCM to give the title compound 403 mg (37%). MS (m/z): 318/320 (M+1/M+3).

Preparation 30 tert-Butyl 2-bromo-6,6-dimethyl-4-oxo-thieno[2,3-c]pyrrole-5-carboxylate

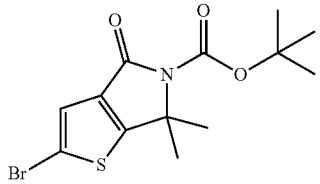 [SMILES: CC(C)(C)OC(=O)N1C(=O)c2cc(Br)sc2C1(C)C]

Treat a solution of 2-bromo-6,6-dimethyl-5H-thieno[2,3-c]pyrrol-4-one (25 g, 102 mmol), N,N-dimethylpyridin-4-amine (1.25 g, 10 mmol), and N,N-diisopropylethylamine (24 mL, 138 mmol) in ACN (481 mL) with di-tert-butyldicarbonate (35 g, 162 mmol). Stir the mixture overnight at room temperature. Add N,N-dimethylpyridin-4-amine (560 mg), N,N-diisopropylethylamine (12 mL) and di-tert-butyl-dicarbonate (12 g) and continue stirring for an additional four hours. Filter the reaction mixture through a silica gel pad and elute the pad with 20% DCM in hexane. Concentrate the filtrate to dryness. Filter the reaction mixture through an additional silica gel pad and elute the pad with 5% DCM in hexanes. Concentrate the filtrate to dryness to give the title compound 31 g (88%) as an orange oil. $^1$H NMR (400.15 MHz, DMSO-$d_6$) δ 7.41 (s, 1H), 1.69 (s, 6H), 1.48 (s, 9H).

Preparation 31

2-Bromo-5-(2-methoxyethyl)-6,6-dimethyl-thieno[2,3-c]pyrrol-4-one

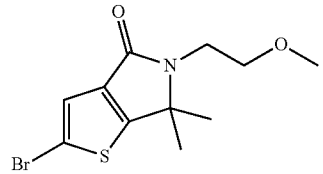 [SMILES: COCCN1C(=O)c2cc(Br)sc2C1(C)C]

Synthetic Method 1:

In a round bottom flask under an atmosphere of nitrogen, dissolve 2-bromo-6,6-dimethyl-5H-thieno[2,3-c]pyrrol-4-one (25 g, 102 mmol) and 2-methoxyethyl bromide (12 mL, 127 mmol) in DMF (250 mL) and cool the reaction mixture to 0° C. Add sodium hydride (60 wt % in mineral oil, 4.469 g, 112 mmol) and allow the reaction to come to room temperature overnight. At room temperature, add additional 2-methoxyethyl bromide (2 mL, 21 mmol) followed by sodium hydride (60 wt % in mineral oil, 1.25 g, 31 mmol). Stir the reaction for 2.5 hours and dilute with water. Extract the resulting solution with three portions EtOAc. Wash the combined organic extracts with a 1:1 saturated NaCl/water solution and then saturated NaCl. Dry the organic solution over anhydrous sodium sulfate, filter and concentrate under reduced pressure. Dry the material under vacuum for two days. Purify the residue by silica gel (1 kg) chromatography eluting with a gradient from 30-50% EtOAc in hexane to provide the title compound 25.78 g (83%) as a light yellow solid. MS (m/z): 304/306 (M+1/M+3).

Synthetic Method 2:

Treat a solution of 2-bromo-6,6-dimethyl-5H-thieno[2,3-c]pyrrol-4-one (150 g, 610 mmol) in 2-methyltetrahydrofuran (1.5 L) with sodium hexamethyldisilylazide (2 M in THF, 405 mL, 810 mmol) over 30 minutes. Add 2-methoxyethyl bromide (190 g, 1372 mmol) over 30 minutes. Heat the reaction at reflux for 18 hours. Add additional 2-methoxyethyl bromide (19 g, 140 mmol) and continue refluxing for an additional six hours. Cool the reaction to room temperature and dilute with EtOAc (2.5 L) and water (2.5 L). Separate the layers and back extract the aqueous solution with EtOAc (2×1.5 L). Combine the organic extracts and wash with saturated NaCl (2×2 L). Dry the organic solution over anhydrous sodium sulfate, filter and concentrate the filtrate under reduced pressure. Purify the residue by silica gel chromatography (700 g) eluting with a gradient from 10 to 25% EtOAc in heptanes to yield 2-bromo-5-(2-methoxyethyl)-6,6-dimethyl-thieno[2,3-c]pyrrol-4-one. Triturate the solid with hexanes (500 mL) at room temperature for 15 minutes, filter and dry the solids to give the title compound 126 g (68%) as a white solid. $^1$H NMR (300 MHz, CDCl$_3$) δ 7.18 (s, 1H), 3.56 (m, 4H), 3.35 (s, 3H), 1.52 (s, 6H).

Preparation 32

2-Bromo-5-[2-(cyclopropoxy)ethyl]-6,6-dimethyl-thieno[2,3-c]pyrrol-4-one

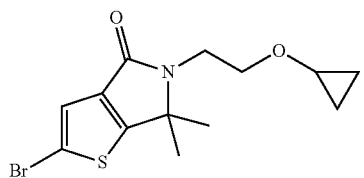 [SMILES: CC1(C)c2sc(Br)cc2C(=O)N1CCOC1CC1]

Treat a solution of 2-bromo-6,6-dimethyl-5H-thieno[2,3-c]pyrrol-4-one (20 g, 81 mmol) in 2-methyltetrahydrofuran (163 mL) with sodium hexamethyldisilylazide (1 M in THF, 100 mL, 100 mmol) over 30 minutes. Add 2-chloroethoxy-cyclopropane (24.5 g, 203 mmol) over 30 minutes. Heat the reaction at reflux for 18 hours. Cool the reaction to room temperature and dilute with EtOAc (500 mL) and saturated aqueous sodium bicarbonate (300 mL). Separate the layers and back extract the aqueous solution with EtOAc (200 mL). Combine the organic extracts and wash with saturated aqueous sodium bicarbonate (300 mL) and saturated NaCl (300 mL). Dry the organic solution over anhydrous sodium sulfate, filter and concentrate the filtrate under reduced pressure. Purify the residue by silica gel chromatography (330 g) eluting with a gradient from 0-5% acetone in DCM to yield the title compound 22 g (82%). MS (m/z): 330/332 (M+1/M+3).

The following compounds are prepared essentially by the method of Preparation 32.

TABLE 5

Preparations 34-37

| Prep. No. | Compound Name | Structure | MS (m/z): |
|---|---|---|---|
| 33 | 2-Bromo-5-[2-[tert-butyl(dimethyl)silyl]oxyethyl]-6,6-dimethyl-thieno[2,3-c]pyrrol-4-one | 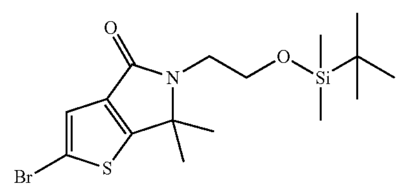 [SMILES: CC1(C)c2sc(Br)cc2C(=O)N1CCO[Si](C)(C)C(C)(C)C] | 404/406 (M + 1/M + 3) |
| 34 | 2'-Bromo-5'-(2-methoxyethyl)spiro[cyclopropane-1,6'-thieno[2,3-c]pyrrole]-4'-one | 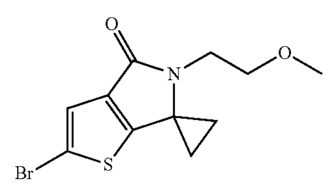 [SMILES: COCCN1C(=O)c2cc(Br)sc2C12CC2] | 302/304 (M + 1/M + 3) |
| 35 | 2'-Bromo-5'-(2-methoxyethyl)spiro[cyclopentane-1,6'-thieno[2,3-c]pyrrole]-4'-one | 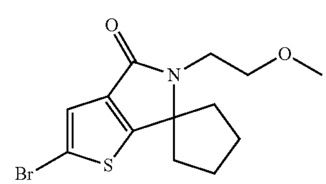 [SMILES: COCCN1C(=O)c2cc(Br)sc2C12CCCC2] | 330/332 (M + 1/M + 3) |
| 36 | 2-Bromo-5-(2-methoxy-propyl)-6,6-dimethyl-thieno[2,3-c]pyrrol-4-one | 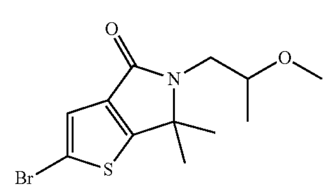 [SMILES: COC(C)CN1C(=O)c2cc(Br)sc2C1(C)C] | 318/320 (M + 1/M + 3) |

Preparation 37

2-(2-Chloro-4-pyridyl)-5-(2-methoxyethyl)-6,6-dimethyl-thieno[2,3-c]pyrrol-4-one

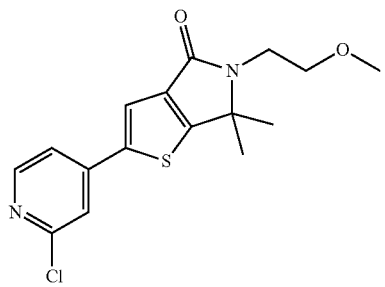 [SMILES: COCCN1C(=O)c2cc(-c3ccnc(Cl)c3)sc2C1(C)C]

Synthetic Method 1:

Combine 2-bromo-5-(2-methoxyethyl)-6,6-dimethyl-thieno[2,3-c]pyrrol-4-one (24.78 g, 81.46 mmol), 2-chloropyridine-4-boronic acid (14.1 g, 89.60 mmol), potassium carbonate (33.8 g, 244.37 mmol), 1,4-dioxane (750 mL) and water (150 mL) in a sealable reaction vessel and degas with nitrogen for 5 minutes. Add tetrakis(triphenylphosphine)palladium (7.060 g, 6.11 mmol) and bubble nitrogen through the reaction mixture for several more minutes. Heat the sealed reaction at 80° C. overnight. Add additional 2-chloropyridine-4-boronic acid (2 g, 12.7 mmol) and tetrakis(triphenylphosphine)palladium (1 g, 0.9 mmol) and maintain heating for an additional 6.5 hours. Add additional 2-chloropyridine-4-boronic acid (2.5 g, 15.9 mmol) and tetrakis(triphenylphosphine)palladium (1 g, 0.9 mmol) and maintain heating for an additional 1.5 hours. Add additional 2-chloropyridine-4-boronic acid (2 g, 12.7 mmol) and tetrakis(triphenylphosphine)palladium (0.4 g, 0.3 mmol) and maintain heating overnight. Add additional 2-chloropyridine-4-boronic acid (2 g, 12.7 mmol) and tetrakis(triphenylphosphine)palladium (0.5 g, 0.5 mmol) and maintain heating for an additional 2 hours. Cool the reaction mixture to room temperature. Dilute the reaction mixture with DCM and wash with water. Back extract the aqueous solution with two portions DCM. Combine the organic solutions and wash with saturated NaCl, dry over anhydrous sodium sulfate, filter and concentrate under reduced pressure. Purify by silica gel (1 kg) chromatography eluting with a gradient from 30-70% EtOAc in hexane to yield 2-(2-chloro-4-pyridyl)-5-(2-methoxyethyl)-6,6-dimethyl-thieno[2,3-c]pyrrol-4-one 13.1 g (48%). MS (m/z): 337 (M+1). Wash the silica gel column with EtOAc to give additional material. Triturate the material with methyl tert-butyl ether and filter to provide the title compound 7.9 g (29%). MS (m/z): 337 (M+1).

Synthetic Method 2:

Treat a solution of 2-bromo-5-(2-methoxyethyl)-6,6-dimethyl-thieno[2,3-c]pyrrol-4-one (200 g, 647 mmol) and 2-chloropyridine-4-boronic acid (143 g, 906 mmol) in EtOH (2 L) with sodium carbonate (2 M in water, 970 mL, 1942 mmol). Sparge the mixture with nitrogen for 15 minutes. Add trans-dichloro-bis-triphenylphosphine palladium (II) (45 g, 64.7 mmol). Sparge the mixture with nitrogen for an additional 15 minutes. Heat the reaction mixture at reflux for 22 hours. Cool the mixture to room temperature and concentrate under reduced pressure. Slurry the resulting solid with water (1 L) at room temperature for 15 minutes and filter. Slurry the resulting solid with methyl tert-butyl ether (2 L) for 15 minutes and filter. Slurry the resulting solid with methyl tert-butyl ether (1 L) for 15 minutes and filter. Dissolve the solid in DCM (1 L) and absorb the mixture onto silica gel (200 g). Elute the mixture through a silica gel column (1.5 kg) eluting with a gradient from 50-80% EtOAc in heptanes to give 2-(2-chloro-4-pyridyl)-5-(2-methoxyethyl)-6,6-dimethyl-thieno[2,3-c]pyrrol-4-one. Triturate the resulting solid in methyl tert-butyl ether (250 mL) for 15 minutes and filter to give the title compound 124.5 g (57%). $^1$H NMR (300 MHz, CDCl$_3$) δ 8.39 (m, 1H), 7.58 (s, 1H), 7.47 (m, 1H), 7.36 (m, 1H), 3.61 (m, 4H), 3.37 (s, 3H), 1.59 (s, 6H). MS (m/z): 337 (M+1).

Synthetic Method 3:

Charge three separate microwave vials each with 2-bromo-5-(2-methoxyethyl)-6,6-dimethyl-thieno[2,3-c]pyrrol-4-one (1 g, 3.3 mmol), 2-chloropyridine-4-boronic acid (580 mg, 3.62 mmol), tris(dibenzylideneacetone)dipalladium(0) (152 mg, 0.16 mmol), tricyclohexylphosphine tetrafluoroborate (363 mg, 0.99 mmol), potassium phosphate tribasic N-hydrate (3.56 g, 16.8 mmol), water (7.6 mL) and 1,4-dioxane (8 mL). Heat the vials in a microwave reactor at 120° C. for 90 minutes. Cool the vials to room temperature and combine the contents of the vials. Dilute the resulting mixture with EtOAc (30 mL) and add anhydrous sodium sulfate. Stir the mixture for 15 minutes and filter the mixture through CELITE®. Wash the solids with EtOAc and concentrate the filtrate under reduced pressure. Purify the residue by silica gel column chromatography by loading the residue onto a 25 g pre-column and eluting the pre-column onto an additional 120 g silica gel column with a gradient from 5-25% acetone in hexanes to give the title compound 2.55 g (77%). MS (m/z): 337 (M+1).

Preparation 38

2-(2-Chloro-4-pyridyl)-5-[2-(cyclopropoxy)ethyl]-6,6-dimethyl-thieno[2,3-c]pyrrol-4-one

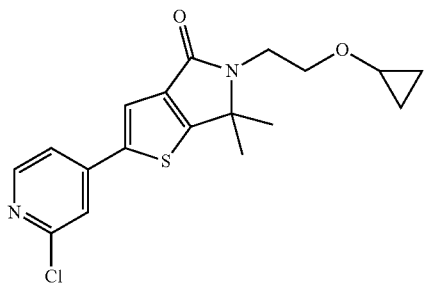 [SMILES: CC1(C)c2sc(-c3ccnc(Cl)c3)cc2C(=O)N1CCOC1CC1]

Treat a solution of 2-bromo-5-[2-(cyclopropoxy)ethyl]-6,6-dimethyl-thieno[2,3-c]pyrrol-4-one (15.8 g, 48 mmol) and 2-chloropyridine-4-boronic acid (10.5 g, 67 mmol) in EtOH (2 L) with sodium carbonate (2 M in water, 50 mL, 100 mmol). Sparge the mixture with nitrogen for 15 minutes. Add trans-dichloro-bis-triphenylphosphine palladium (II) (1.0 g, 1.4 mmol). Sparge the mixture with nitrogen for an additional 15 minutes. Heat the reaction mixture at 60° C. for five hours. Add additional 2-chloropyridine-4-boronic acid (2.2 g) and heat the reaction at 80° C. for an additional two hours. Cool the mixture to room temperature and dilute with EtOAc (200 mL). Wash the organic solution with saturated NaCl. Concentrate the organic solution under reduced pressure. Purify the residue by silica gel chromatography (220 g) eluting with a gradient from 0-10%/o acetone in DCM to yield the title compound 12.9 g (74%). MS (m/z): 363 (M+1).

The following compounds are prepared essentially by the method of Preparation 38.

TABLE 6

Preparations 40-46

| Prep. No. | Compound Name | Structure | MS (m/z): (M + 1) |
|---|---|---|---|
| 39 | 5-[2-[tert-Butyl(dimethyl)silyl]oxyethyl]-2-(2-chloro-4-pyridyl)-6,6-dimethyl-thieno[2,3-c]pyrrol-4-one | 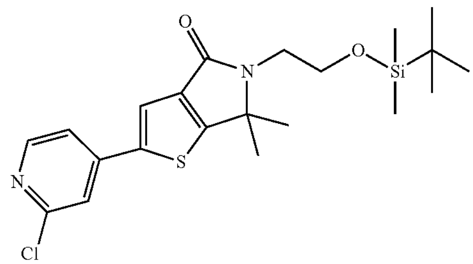 [SMILES: CC1(C)c2sc(-c3ccnc(Cl)c3)cc2C(=O)N1CCO[Si](C)(C)C(C)(C)C] | 437 (M + 1) |
| 40 | tert-Butyl 2-(2-chloro-4-pyridyl)-6,6-dimethyl-4-oxo-thieno[2,3-c]pyrrole-5-carboxylate | 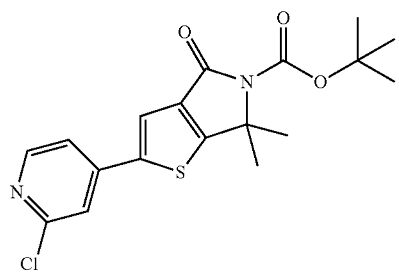 [SMILES: CC(C)(C)OC(=O)N1C(=O)c2cc(-c3ccnc(Cl)c3)sc2C1(C)C] | 379 (M + 1) |
| 41 | 2-(2-Chloro-4-pyridyl)-6-ethyl-5-(2-methoxyethyl)-6-methyl-thieno[2,3-c]pyrrol-4-one | 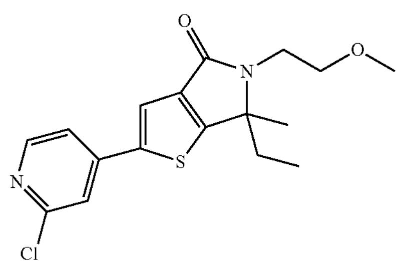 [SMILES: CCC1(C)c2sc(-c3ccnc(Cl)c3)cc2C(=O)N1CCOC] | 351 (M + 1) |
| 42 | 2'-(2-Chloro-4-pyridyl)-5'-(2-methoxyethyl)spiro[cyclopropane-1,6'-thieno[2,3-c]pyrrole]-4'-one | 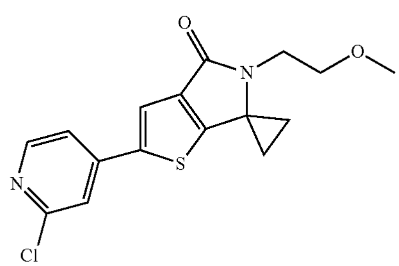 [SMILES: COCCN1C(=O)c2cc(-c3ccnc(Cl)c3)sc2C12CC2] | 335 (M + 1) |
| 43 | 2'-(2-Chloro-4-pyridyl)-5'-(2-methoxyethyl)spiro[cyclopentane-1,6'-thieno[2,3-c]pyrrole]-4'-one | 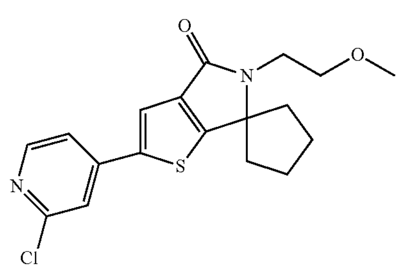 [SMILES: COCCN1C(=O)c2cc(-c3ccnc(Cl)c3)sc2C12CCCC2] | 363 (M + 1)) |

TABLE 6-continued

Preparations 40-46

| Prep. No. | Compound Name | Structure | MS (m/z): (M + 1) |
|---|---|---|---|
| 44 | 2-(2-Chloro-4-pyridyl)-5-(2-methoxypropyl)-6,6-dimethyl-thieno[2,3-c]pyrrol-4-one | 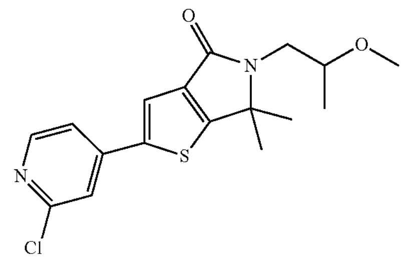 [SMILES: COC(C)CN1C(=O)c2cc(-c3ccnc(Cl)c3)sc2C1(C)C] | 351 (M + 1) |
| 45 | 2-(2-Chloro-4-pyridyl)-5-(2-methoxyethyl)-6-methyl-6H-thieno[2,3-c]pyrrol-4-one | 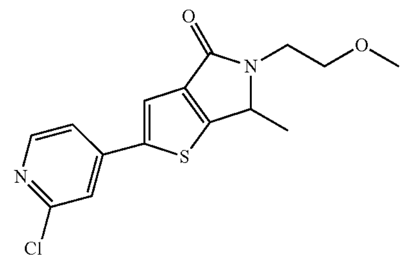 [SMILES: COCCN1C(=O)c2cc(-c3ccnc(Cl)c3)sc2C1C] | 323 (M + 1) |

Preparation 46

2-(2-Chloro-4-pyridyl)-6,6-dimethyl-5H-thieno[2,3-c]pyrrol-4-one

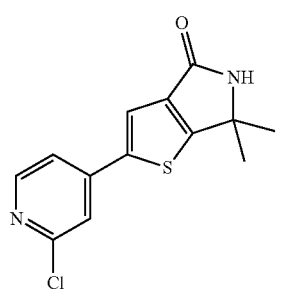 [SMILES: CC1(C)NC(=O)c2cc(-c3ccnc(Cl)c3)sc21]

Treat a solution of tert-butyl 2-(2-chloro-4-pyridyl)-6,6-dimethyl-4-oxo-thieno[2,3-c]pyrrole-5-carboxylate (7.38 g, 19.5 mmol) in DCM (56 mL) with trifluoroacetic acid (65 mL, 859 mmol) and stir the mixture for two hours. Concentrate the mixture to dryness. Add DCM and saturated aqueous sodium bicarbonate and separate layers. Back extract the aqueous layer with additional DCM. Combine the organic extracts and dry over anhydrous sodium sulfate. Filter and concentrate the filtrate under reduced pressure. Purify the residue by silica gel column chromatography by loading the product onto a 65 g loading column and eluting the column onto a 220 g column with a gradient from 0-70% ACN in DCM to give the title compound 2 g (37%). MS (m/z): 279 (M+1).

Preparation 47

2-(2-Chloro-4-pyridyl)-5-[(2R)-2-hydroxypropyl]-6,6-dimethyl-thieno[2,3-c]pyrrol-4-one

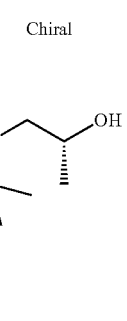

Heat a solution of 2-(2-chloro-4-pyridyl)-6,6-dimethyl-5H-thieno[2,3-c]pyrrol-4-one (450 mg, 1.6 mmol), (R)-(+)-propylene oxide (1.13 mL, 16.1 mmol), and triethylamine (1.13 mL, 8.1 mmol) in DMF (2.78 mL) in a sealed tube at 120° C. overnight. Cool the mixture to room temperature and dilute the mixture with EtOAc. Wash the organic solution with three portions 5% aqueous lithium chloride solution. Combine the aqueous solutions and back extract with EtOAc. Combine the organic extracts and dry over sodium sulfate. Filter the mixture and concentrate the filtrate to dryness. Purify the residue by silica gel column chromatography on a 24 g column with a gradient from 70-100% EtOAc in DCM to give the title compound 395 mg (73%). MS (m/z): 337 (M+1).

Preparation 48

2-(2-Chloro-4-pyridyl)-5-(2R)-2-methoxypropyl)-6,6-dimethyl-thieno[2,3-c]pyrrol-4-one Chiral

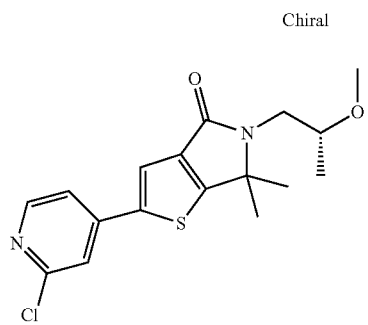 [SMILES: CO[C@H](C)CN1C(=O)c2cc(-c3ccnc(Cl)c3)sc2C1(C)C]

Cool a solution of 2-(2-chloro-4-pyridyl)-5-[(2R)-2-hydroxypropyl]-6,6-dimethyl-thieno[2,3-c]pyrrol-4-one (415 mg, 1.2 mmol) in THF (8 mL) in an ice water bath. Treat the mixture with sodium hydride (60 wt/o suspension in mineral oil, 79 mg, 1.3 mmol) and stirred at this temperature for 15 minutes. Treat the mixture with methyl iodide (307 μL, 4.9 mmol), remove the ice water bath and stir the mixture overnight. Concentrate the mixture under reduced pressure to dryness. Treat the residue with DCM and filter the mixture to remove the solids. Wash the solids with additional DCM and concentrate the filtrate under reduced pressure to dryness. Purify the residue by silica gel column chromatography on a 24 g column with a gradient from 30-70% EtOAc in hexane to give the title compound 379 mg (88%). MS (m/z): 351 (M+1).

Preparation 49

2-(2-Chloro-4-pyridyl)-5-[2-(cyclopropoxy)ethyl]-6,6-dimethyl-thieno[2,3-c]pyrrol-4-one

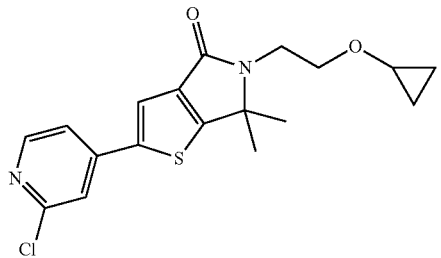 [SMILES: CC1(C)c2sc(-c3ccnc(Cl)c3)cc2C(=O)N1CCOC1CC1]

Cool a solution of 2-(2-chloro-4-pyridyl)-6,6-dimethyl-5H-thieno[2,3-c]pyrrol-4-one (500 mg, 1.8 mmol) in DMF (18 mL) in an ice water bath. Treat the mixture with sodium hydride (60 wt % suspension in mineral oil, 108 mg, 2.7 mmol) and stirred at this temperature for 15 minutes. Treat the mixture with 2-iodoethoxycyclopropane (761 mg, 3.6 mmol), remove the ice water bath and stir the mixture for four hours. Quench the reaction with EtOAc and saturated NaCl. Wash the organic solution with several portions saturated NaCl and then dry over anhydrous sodium sulfate. Filter the solution and wash the solid with EtOAc. Concentrate the filtrate under reduced pressure to give the title compound 651 mg (99%). MS (m/z): 363 (M+1).

Preparation 50

2-(2-Chloro-4-pyridyl)-5-[2-(2,2-difluoroethoxy)ethyl]-6,6-dimethyl-thieno[2,3-c]pyrrol-4-one

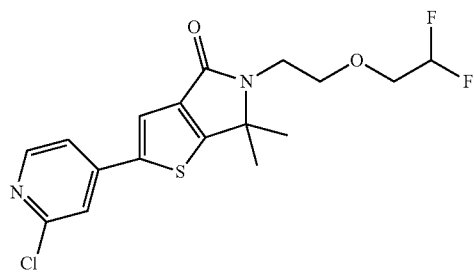 [SMILES: CC1(C)c2sc(-c3ccnc(Cl)c3)cc2C(=O)N1CCOCC(F)F]

Cool a solution of 2-(2-chloro-4-pyridyl)-6,6-dimethyl-5H-thieno[2,3-c]pyrrol-4-one (500 mg, 1.8 mmol) in DMF (18 mL) in an ice water bath. Treat the mixture with sodium hydride (60 wt % suspension in mineral oil, 108 mg, 2.7 mmol) and stir at this temperature for 15 minutes. Treat the mixture with 2-(2-bromoethoxy)-1,1-difluoroethane (678 mg, 3.6 mmol), remove the ice water bath and stir the mixture overnight. Quench the reaction with water and collect the resulting precipitate. Wash the solid with water and diethyl ether to give the title compound 625 mg (90%). MS (m/z): 387 (M+1).

The following compounds are prepared essentially by the method of Preparation 50.

TABLE 7

Preparations 51-53

| Prep. No. | Compound Name | Structure | MS (m/z): (M + 1) |
|---|---|---|---|
| 51 | 2-(2-Chloro-4-pyridyl)-5-(2-methoxyethyl)-6,6-dimethyl-thieno[2,3-c]pyrro-4-one | 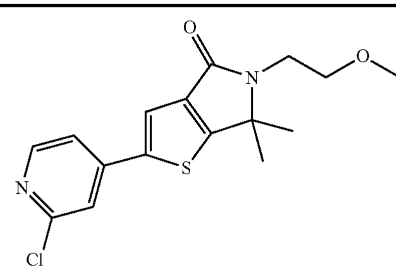 | 337 (M + 1) |

TABLE 7-continued

Preparations 51-53

| Prep. No. | Compound Name | Structure | MS (m/z): (M + 1) |
|---|---|---|---|
| 52 | 2-(2-Chloro-4-pyridyl)-6,6-dimethyl-5-[2-(trideuteriomethoxy)ethyl]thieno[2,3-c]pyrrol-4-one | 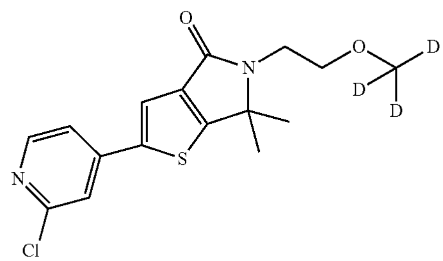 [SMILES: [2H]C([2H])([2H])OCCN1C(=O)c2cc(-c3ccnc(Cl)c3)sc2C1(C)C] | 340 (M + 1) |
| 53 | 2-(2-Chloro-4-pyridyl)-6,6-dimethyl-5-[2-(trifluoromethoxy)ethylithieno[2,3-c]pyrrol-4-one | 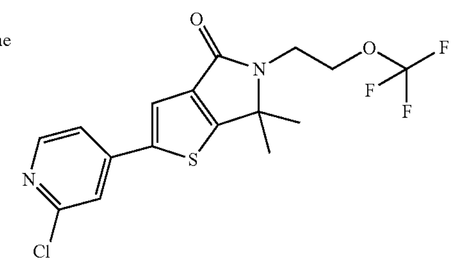 | 391 (M + 1) |

Preparation 54

4-Chloro-N-(2-methylpyrazol-3-yl)pyridin-2-amine

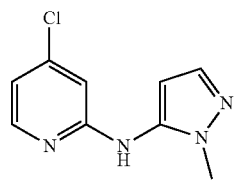

Heat a solution of 2,4-dichloropyridine (15.3 g, 103 mmol), 1-methyl-5-aminopyrazole (11 g, 113 mmol), cesium carbonate (6 g, 10 mmol) and tris(dibenzylideneacetone)dipalladium(0) (4.7 g, 5 mmol) in 1,4-dioxane (750 mL) in a sealed vessel at 75° C. overnight. Cool the reaction to room temperature and dilute with water (1.5 L). Extract the mixture with three portions DCM. Filter the aqueous layer to remove solids and extract the filtrate with two portions EtOAc. Combine all organic extracts, dry over magnesium sulfate, filter and concentrate the filtrate. Purify the residue by silica gel column chromatography by loading the product onto a 260 g pre-column and eluting the pre-column onto a 750 g column with a gradient from 1-5% MeOH in DCM to give the title compound 16.8 g (78%). MS (m/z): 209 (M+1).

Preparation 55 tert-Butyl 6,6-dimethyl-2-[2-[(2-methylpyrazol-3-yl)amino]-4-pyridyl]-4-oxo-thieno[2,3-c]pyrrole-5-carboxylate

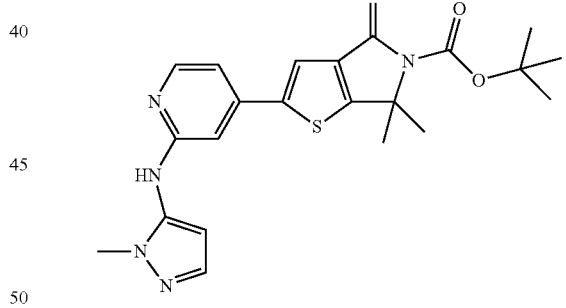

Heat a solution of tert-butyl 2-(2-chloro-4-pyridyl)-6,6-dimethyl-4-oxo-thieno[2,3-c]pyrrole-5-carboxylate (400 mg, 1.06 mmol), 1-methyl-5-aminopyrazole (308 mg, 3.17 mmol), cesium carbonate (1.03 g, 3.17 mmol), palladium (II)acetate (9 mg, 0.04 mmol) and 4,5-bis(diphenylphosphino)-9,9-dimethylxanthene (37 mg, 0.06 mmol) in 1,4-dioxane (8 mL) in a sealed vessel at 95° C. for 16 hours. Add 1-methyl-5-aminopyrazole (103 mg, 1.06 mmol), cesium carbonate (334 mg, 1.06 mmol), palladium(II)acetate (9 mg, 0.04 mmol) and 4,5-bis(diphenylphosphino)-9,9-dimethylxanthene (37 mg, 0.06 mmol). Heat the mixture at 95° C. overnight. Cool the reaction to room temperature and dilute with water and DCM. After separating the layers, extract the aqueous layer with 10% MeOH in DCM. Combine the organic extracts and concentrate under reduced pressure. Purify the residue by silica gel column chromatography by loading the product onto a 5 g loading column and eluting the column onto a 40 g column with a gradient from 5-15% MeOH in DCM to give the title compound 75 mg (16%). MS (m/z): 440 (M+1).

EXAMPLE 1

5-(2-Methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one

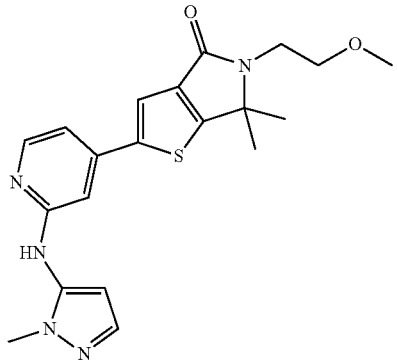

Synthetic Method 1:

In two screw-top glass pressure vessels, split and combine the following amounts in two equal portions 2-(2-chloro-4-pyridyl)-5-(2-methoxyethyl)-6,6-dimethyl-thieno[2,3-c]pyrrol-4-one (13 g, 38.59 mmol), 1-methyl-5-aminopyrazole (11.245 g, 115.78 mmol), cesium carbonate (37.724 g, 115.78 mmol), 4,5-bis(diphenylphosphino)-9,9-dimethylxanthene (2.010 g, 3.47 mmol), palladium(II)acetate (520 mg, 2.32 mmol) and 1,4-dioxane (350 mL). Seal each vessel and heat at 110° C. overnight. Dilute the reaction mixture with 10% MeOH in DCM (2 L) and wash the resulting solution with saturated NaCl. Back extract the aqueous solution with DCM and combine the organic solutions. Dry the combined solutions over a mixture of anhydrous sodium sulfate and anhydrous magnesium sulfate, filter and concentrate the filtrate under reduced pressure. Purify by silica gel chromatography by loading the residue onto a 260 g loading column with DCM and then eluting the loading column onto a 750 g silica gel column with a gradient of 60-100% of 10% MeOH in EtOAc in hexane to yield the title compound 8.4 g (55%). MS (m/z): 398 (M+1).

Synthetic Method 2:

Sparge a solution of 2-(2-chloro-4-pyridyl)-5-(2-methoxyethyl)-6,6-dimethyl-thieno[2,3-c]pyrrol-4-one (100 g, 298 mmol), 1-methyl-5-aminopyrazole (43 g, 446 mmol), and sodium tert-butoxide (57 g, 595 mmol) in toluene (1.5 L) with nitrogen for 15 minutes. Treat the resulting mixture with (R)-1-[(S$_P$)-2-(dicyclohexylphosphino)ferrocenyl]ethyldi-tert-butylphosphine (1.61 g, 3 mmol) and bis(tri-o-tolylphosphine)palladium(0) (2.12 g, 3 mmol). Sparge the mixture with nitrogen for an additional 15 minutes and reflux for three hours. Cool the reaction to 10° C. and collect the resulting solid by filtration. Dissolve the solid in DCM (4 L) and wash with half saturated aqueous sodium bicarbonate (2 L). Dry the organic solution over sodium sulfate, filter and concentrate the filtrate under reduced pressure. Slurry the solid with diethyl ether (500 mL) for 30 minutes and then filter. Dissolve the solid in DCM (1 L) and absorb onto silica gel (300 g). Elute the mixture onto a silica gel column (600 g) with 5% MeOH in DCM to give 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one 107 g (82%). Several batches of the product are produced using the above method with one batch differing in the base (potassium carbonate) used. Dissolve the combined batches of 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one (254 g) in DCM (2.5 L). Treat the solution with SiliaMetS® Thiol (75 g, 1.28 mmol/g, 40-63 micron) and stir the reaction for 18 hours. Filter the mixture to remove the solids and treat the filtrate with a second portion of SiliaMetS® Thiol (75 g, 1.28 mmol/g, 40-63 micron). Stir the mixture for an additional 18 hours. Filter to remove the solid and concentrate the filtrate under reduced pressure. Triturate the resulting solid in toluene (600 mL) at 40° C. for 30 minutes. Collect the solid by vacuum filtration. Triturate the resulting solid in toluene (300 mL) at 40° C. for 30 minutes. Collect the solid by vacuum filtration and dry under vacuum at 30° C. for 14 hours to give the title compound 223 g. $^1$H NMR (300 MHz, CDCl$_3$) δ 8.15 (d, 1H), 7.54 (d, 1H), 7.46 (s, 1H), 7.02 (brs, 1H), 6.95 (m, 1H), 6.63 (d, 1H), 6.19 (d, 1H), 3.79 (s, 3H), 3.60 (m, 4H), 3.36 (s, 3H), 1.56 (s, 6H). MS (m/z): 398 (M+1).

EXAMPLE 1, CRYSTALLINE FORM 1

5-(2-Methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one (Crystalline Form 1)

In a round bottom flask, slurry 5-(2-methoxyethyl)-6,6-dimethyl-2-{2-[(l-methyl-1H-pyrazol-5-yl)amino]pyridin-4-yl}-5,6-dihydro-4H-thieno[2,3-c]pyrrol-4-one (15.31 g) in MeOH and EtOAc with a minimum amount of DCM and heat on a rotary evaporator until the material goes into solution with as little solvent as possible. Concentrate the solution to dryness. Dilute the resulting solid with EtOAc and a small amount of MeOH until the slightly colored solid precipitate flows freely. Dilute the solution with ether and hexanes and spin on a rotary evaporator. Triturate the slurry in a sonicator and then allow the slurry to stand. Collect the solid by vacuum filtration and wash with ether and hexanes. Dry the solid in a vacuum oven to provide the title compound 14.1 g.

EXAMPLE 1, CRYSTALLINE FORM 2

5-(2-Methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one (Crystalline Form 2)

Heat 5-(2-methoxyethyl)-6,6-dimethyl-2-{2-[(1-methyl-1H-pyrazol-5-yl)amino]pyridin-4-yl}-5,6-dihydro-4H-thieno[2,3-c]pyrrol-4-one (223 g) in EtOH (200 proof, 1200 mL) and water (400 mL) at 60° C. until a clear solution persists. Cool the solution to 45-50° C. and dilute the solution with water (1600 mL) over one hour. Cool the mixture to room temperature and collect the solid by vacuum filtration. Dry the resulting solid at 35° C. under vacuum for 18 hours to give the title compound 209 g.

EXAMPLE 2

5-[2-(Cyclopropyloxy)ethyl]-6,6-dimethyl-2-{2-[(1-methyl-1H-pyrazol-5-yl)amino]pyridin-4-yl}-5,6-dihydro-4H-thieno[2,3-c]pyrrol-4-one

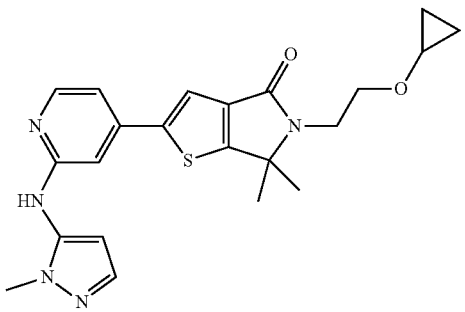 [SMILES: Cn1nccc1Nc1cc(-c2cc3c(s2)C(C)(C)N(CCOC2CC2)C3=O)ccn1]

Synthetic Method 1:

In a glass pressure vessels, combine 2-(2-chloro-4-pyridyl)-5-[2-(cyclopropoxy)ethyl]-6,6-dimethyl-thieno[2,3-c]pyrrol-4-one (350 mg, 0.96 mmol), 1-methyl-5-aminopyrazole (187 mg, 1.9 mmol), cesium carbonate (943 mg, 2.9 mmol), 4,5-bis(diphenylphosphino)-9,9-dimethylxanthene (84 mg, 0.14 mmol) and 1,4-dioxane (8 mL). Degas the mixture for 15 minutes and add palladium(II)acetate (22 mg, 0.1 mmol). Seal the vessel and heat at 90° C. overnight. Filter the mixture through CELITE® and wash through with EtOAc and DCM. Concentrate the filtrate. Purify the residue by reverse phase chromatography (100 g REDISEP RF GOLD® High Performance C18 Reverse Phase Column, 5-100% Formic Acid/ACN in Formic Acid/Water, 30 Column Volume Gradient). Concentrate the appropriate fractions to a minimum volume and partition the resulting aqueous solution between DCM and saturated aqueous sodium bicarbonate. Separate the layers and dry the organic solution over sodium sulfate. Filter the solution and concentrate the filtrate under reduced pressure. Vacuum dry the residue at 50° C. for one hour to give the title compound 247 mg (60%). MS (m/z): 424 (M+1).

Synthetic Method 2:

Sparge a solution of 2-(2-chloro-4-pyridyl)-5-[2-(cyclopropoxy)ethyl]-6,6-dimethyl-thieno[2,3-c]pyrrol-4-one (13.9 g, 121 mmol), 1-methyl-5-aminopyrazole (11 g, 113 mmol), and sodium tert-butoxide (6.5 g, 68 mmol) in toluene (150 mL) with nitrogen for 15 minutes. Treat the resulting mixture with (R)-1-[(Sp)-2-(dicyclohexylphosphino)ferrocenyl]ethyldi-tert-butylphosphine (200 mg, 0.36 mmol) and bis(tri-o-tolylphosphine)palladium(0) (250 mg, 0.35 mmol). Heat the reaction mixture to reflux for one hour. Cool the reaction to room temperature and dilute with EtOAc (500 mL). Wash the organic solution with water (300 mL). Separate and concentrate the organic phase under reduced pressure. Dissolve the residue in DCM (150 mL) and treat the solution with SILIAMETS® Thiol (40 g, 1.28 mmol/g, 40-63 micron) and stir the mixture for four hours. Filter to remove the solid and concentrate the filtrate under reduced pressure to give the title compound 11.1 g (86%). MS (m/z): 424 (M+1).

The following compounds are prepared essentially by the methods of Example 2.

Alterations in catalyst, ligand and/or base are indicated.

TABLE 8

Examples 3-24

| Example No. | Compound Name | Structure | MS (m/z): | Comments |
|---|---|---|---|---|
| 3 | 5-(2-Hydroxyethyl)-6,6-dimethyl-2-{2-[(1-methyl-1H-pyrazol-5-yl)amino]pyridin-4-yl}-5,6-dihydro-4H-thieno[2,3-c]pyrrol-4-one | 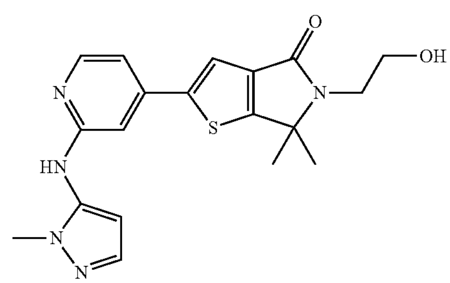 [SMILES: Cn1nccc1Nc1cc(-c2cc3c(s2)C(C)(C)N(CCO)C3=O)ccn1] | 384 (M + 1) | Bis(tri-o-tolylphosphine)palladium(0), (R)-1-[(S)-2-(Dicyclohexylphosphino)ferrocenyl]ethyldi-tert-butylphosphine. Sodium tert-butoxide |
| 4 | 5'-(2-Methoxyethyl)-2'-{2-[(1-methyl-1H-pyrazol-5-yl)amino]pyridin-4-yl}spiro[cyclopropane-1,6'-thieno[2,3-c]pyrrol]-4'(5'H)-one | 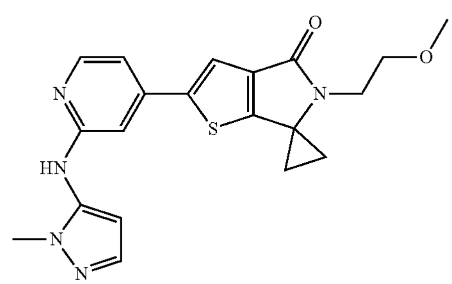 | 396 (M + 1) | Cesium carbonate |

TABLE 8-continued

Examples 3-24

| Example No. | Compound Name | Structure | MS (m/z): | Comments |
|---|---|---|---|---|
| 5 | 5'-(2-Methoxyethyl)-2'{2-[(1-methyl-1H-pyrazol-5-yl)amino]pyridin-4-yl}spiro[cyclopentane-1,6'-thieno[2,3-c]pyrrol]-4'(5')-one | 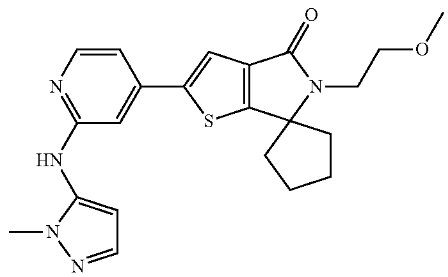 | 424 (M + 1) | Cesium carbonate |
| 6 | 2-(2-{[1-(2-Fluoroethyl)-1H-pyrazol-5-yl]amino}pyridin-4-yl)-5-(2-methoxyethyl)-6,6-dimethyl-5,6-dihydro-4H-thieno[2,3-c]pyrrol-4-one | 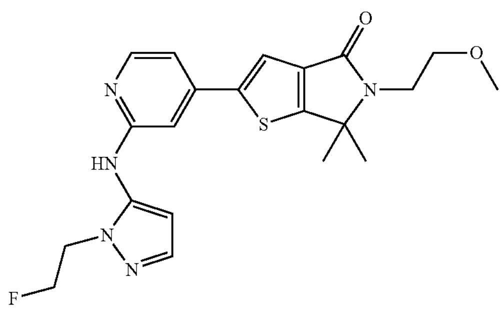 [SMILES: COCCN1C(=O)c2cc(-c3ccnc(Nc4ccnn4CCF)c3)sc2C1(C)C] | 430 (M + 1) | Tris(dibenzylidene-acetone)dipalladium(0), Cesium carbonate |
| 7 | 5-[2-(2,2-Difluoroethoxy)ethyl]-6,6-dimethyl-2-{2-[(1-methyl-1H-pyrazol-5-yl)amino]pyridin-4-yl}-5,6-dihydro-4H-thieno[2,3-c]pyrrol-4-one | 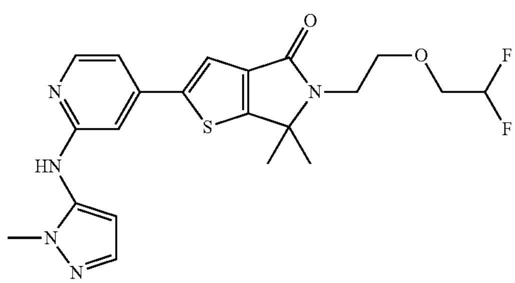 [SMILES: Cn1nccc1Nc1cc(-c2cc3c(s2)C(C)(C)N(CCOCC(F)F)C3=O)ccn1] | 448 (M + 1) | Chloro[2-(di-tert-butylphosphino)-2',4',6'-triisopropyl-1,1'-biphenyl]2-(2-aminoethyl)phenyl)]palladium(II), 2-(Di-tert-butylphosphino)-2',4',6'-triisopropyl-1,1'-biphenyl][2-(2-aminoethyl)phenyl), potassium tert-butoxide |
| 8 | 5-(2-Methoxyethyl)-6,6-dimethyl-2-[2-(1H-pyrazol-5-ylamino)pyridin-4-yl]-5,6-dihydro-4H-thieno[2,3-c]pyrrol-4-one | 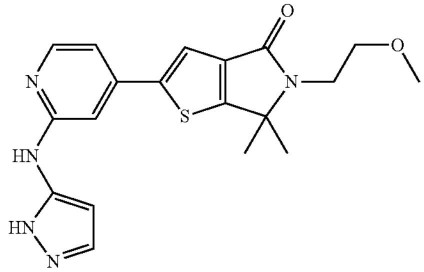 [SMILES: COCCN1C(=O)c2cc(-c3ccnc(Nc4ccn[nH]4)c3)sc2C1(C)C] | 384 (M + 1) | Tris(dibenzylidene-acetone)dipalladium(0), Cesium carbonate |

TABLE 8-continued

Examples 3-24

| Example No. | Compound Name | Structure | MS (m/z): | Comments |
|---|---|---|---|---|
| 9 | 6,6-Dimethyl-2-[2-[(2-methylpyrazol-3-yl)amino]-4-pyridyl]-5-[-2-(trideuteriomethoxy)ethyl]thieno[2,3-c]pyrrol-4-one | 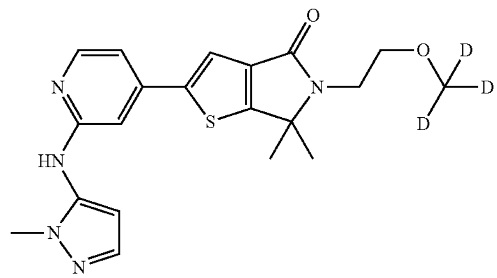 [SMILES: [2H]C([2H])([2H])OCCN1C(=O)c2cc(-c3ccnc(Nc4ccnn4C)c3)sc2C1(C)C] | 401 (M + 1) | Cesium carbonate |
| 10 | 2-(2-{[1-(2,2-Difluoroethyl)-1H-pyrazol-5-yl]amino}pyridin-4-yl)-5-(2-methoxyethyl)-6,6-dimethyl-5,6-dihydro-4H-thieno[2,3-c]pyrrol-4-one | 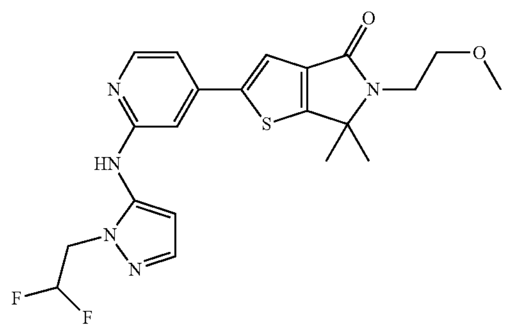 [SMILES: COCCN1C(=O)c2cc(-c3ccnc(Nc4ccnn4CC(F)F)c3)sc2C1(C)C] | 448 (M + 1) | Cesium carbonate |
| 11 | 5-(2-Methoxyethyl)-6,6-dimethyl-2-(2-{[1-(2,2,2,-trifluoroethyl)-1H-pyrazol-5-yl]amino}pyridin-4-yl)-5,6-dihydro-4H-thieno[2,3-c]pyrrol-4-one | 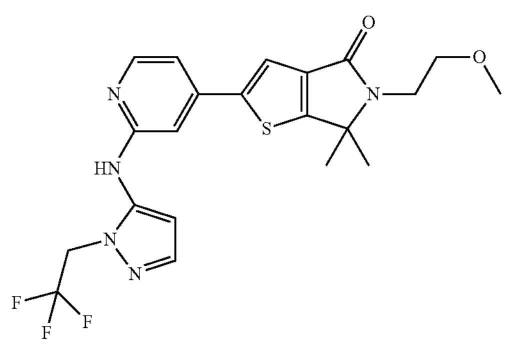 [SMILES: COCCN1C(=O)c2cc(-c3ccnc(Nc4ccnn4CC(F)(F)F)c3)sc2C1(C)C] | 466 (M + 1) | Cesium carbonate |
| 12 | 5-(2-Methoxyethyl)-2-(2-{[1-(2-methoxyethyl)-1H-pyrazol-5-yl]amino}pyridin-4-yl)-6,6-dimethyl-5,6-dihydro-4H-thieno[2,3-c]pyrrol-4-one | 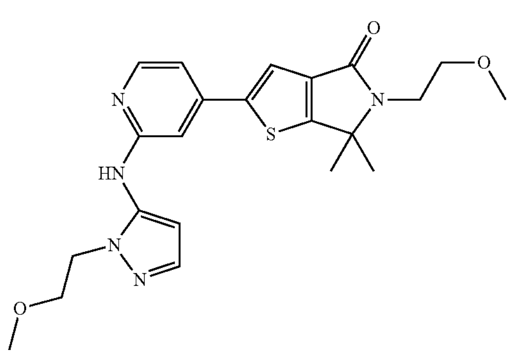 | 442 (M + 1) | Cesium carbonate |

TABLE 8-continued

Examples 3-24

| Example No. | Compound Name | Structure | MS (m/z): | Comments |
|---|---|---|---|---|
| 13 | 2-{2-[(1,3-Dimethyl-1H-pyrazol-5-yl)amino]pyridin-4-yl}-5-(2-methoxyethyl)-6,6-dimethyl-5,6-dihydro-4H-thieno[2,3-c]pyrrol-4-one | 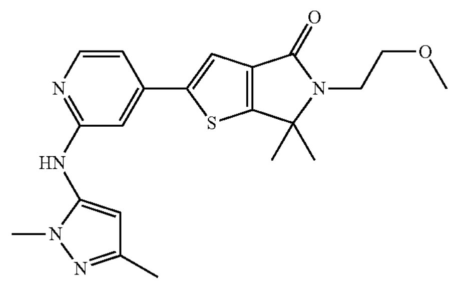 | 412 (M + 1) | Cesium carbonate |
| 14 | 2-{2-[(3-Cyclopropyl-1-methyl-1H-pyrazol-5-yl)amino]pyridin-4-yl}-5-(2-methoxyethyl)-6,6-dimethyl-5,6-dihydro-4H-thieno[2,3-c]pyrrol-4-one | 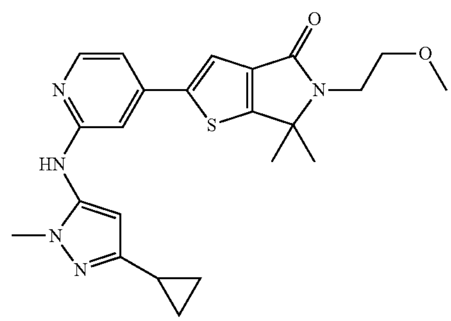 | 438 (M + 1) | Cesium carbonate |
| 15 | 6,6-Dimethyl-2-{2-[(1-methyl-1H-pyrazol-5-yl)amino]pyridin-4-yl}-[2-(trifluoromethoxy)ethyl]-5,6-dihydro-4H-thieno[2,3-c]pyrrol-4-one | 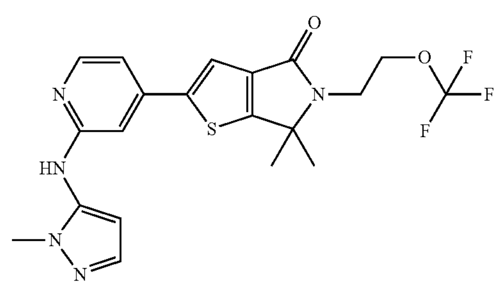 [SMILES: Cn1nccc1Nc1cc(-c2cc3c(s2)C(C)(C)N(CCOC(F)(F)F)C3=O)ccn1] | 452 (M + 1) | Cesium carbonate |
| 16 | 5-(2-Methoxyethyl)-6,6-dimethyl-2-(2-{[1-(propan-2-yl)-1H-pyrazol-5-yl]amino}pyridin-4-yl)-5,6-dihydro-4H-thieno[2,3-c]pyrrol-4-one | 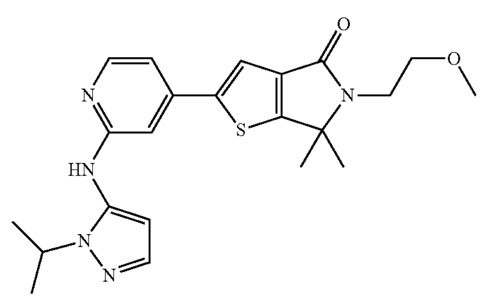 [SMILES: COCCN1C(=O)c2cc(-c3ccnc(Nc4ccnn4C(C)C)c3)sc2C1(C)C] | 426 (M + 1) | Cesium carbonate |
| 17 | 2-(2-{[1-(difluoromethyl)-1H-pyrazol-5-yl]amino}pyridin-4-yl)-5-(2-methoxyethyl)-6,6-dimethyl-5,6-dihydro-4H-thieno[2,3-c]pyrrol-4-one | 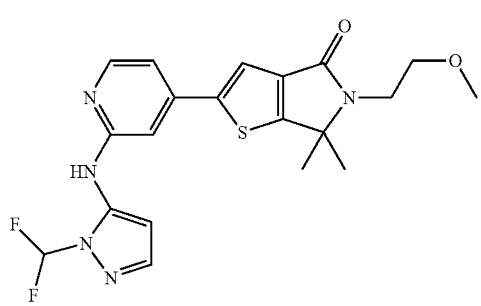 [SMILES: COCCN1C(=O)c2cc(-c3ccnc(Nc4ccnn4C(F)F)c3)sc2C1(C)C] | 434 (M + 1) | Cesium carbonate |

TABLE 8-continued

Examples 3-24

| Example No. | Compound Name | Structure | MS (m/z): | Comments |
|---|---|---|---|---|
| 18 | 2-{2-[(1-Ethyl-1H-pyrazol-5-yl)amino]pyridin-4-yl}-5-(2-methoxyethyl)-6,6-dimethyl-5,6-dihydro-4H-thieno[2,3-c]pyrrol-4-one | 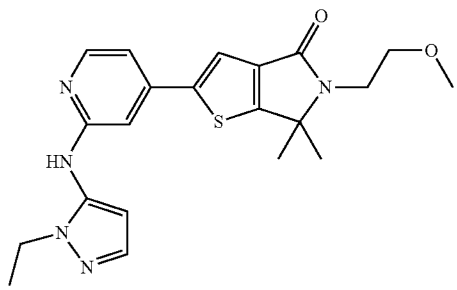 [SMILES: CCn1nccc1Nc1cc(-c2cc3c(s2)C(C)(C)N(CCOC)C3=O)ccn1] | 412 (M + 1) | Chloro[2-(di-tert-butylphosphino)-2',4',6'-triisopropyl-1,1'-biphenyl][2-(2-aminoethyl)phenyl)]palladium (II), 2-(Di-tert-butylphosphino)-2',4',6'-triisopropyl-1,1'-biphenyl][2-(2-aminoethyl)phenyl), potassium tert-butoxide |
| 19 | 2-{2-[(1-Cyclopropyl-1H-pyrazol-5-yl)amino]pyridin-4-yl}-5-(2-methoxyethyl)-6,6-dimethyl-5,6-dihydro-4H-thieno[2,3-c]pyrrol-4-one | 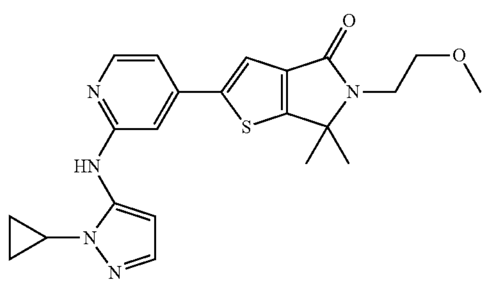 [SMILES: COCCN1C(=O)c2cc(-c3ccnc(Nc4ccnn4C4CC4)c3)sc2C1(C)C] | 424 (M + 1) | Cesium carbonate |
| 20 | 6-Ethyl-5-(2-methoxyethyl)-6-methyl-2-{2-[(1-methyl-2-1H-pyrazol-5-yl)aminolpyridin-4-yl}-5,6-dihydro-4H-thieno[2,3-c]pyrrol-4-one | 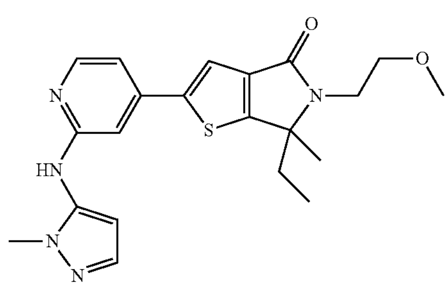 | 412 (M + 1) | Cesium carbonate |
| 21 | 5-(2-Methoxypropyl)-6,6-dimethyl-2-{2-[(1-methyl-1H-pyrazol-5-yl)aminolpyridin-4-yl}-5,6-dihydro-4H-thieno[2,3-c]pyrrol-4-one | 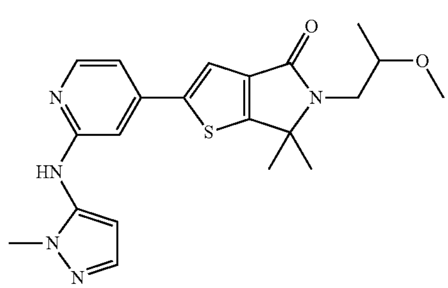 | 412 (M + 1) | Cesium carbonate |

TABLE 8-continued

Examples 3-24

| Example No. | Compound Name | Structure | MS (m/z): | Comments |
|---|---|---|---|---|
| 22 | 5-[(2R)-2-Methoxypropyl]-6,6-dimethyl-2-{2-[(1-methyl-1H-pyrazol-5-yl)amino]pyridin-4-yl}-5,6-dihydro-4H-thieno[2,3-c]pyrrol-4-one | Chiral | 412 (M + 1) | Chloro[2-(di-tert-butylphosphino)-2',4',6'-triisopropyl-1,1'-biphenyl][2-(2-aminoethyl)phenyl)]palladium(II), 2-(Di-tert-butylphosphino)-2',4',6'-triisopropyl-1,1'-biphenyl][2-(2-aminoethyl)phenyl), potassium tert-butoxide |
| 23 | 5-[(2S)-2-Methoxypropyl]-6,6-dimethyl-2-{2-[(1-methyl-1H-pyrazol-5-yl)amino]pyridin-4-yl}-5,6-dihydro-4H-thieno[2,3-c]pyrrol-4-one | Chiral | 412 (M + 1) | Chloro[2-(di-tert-butylphosphino)-2',4',6'-triisopropyl-1,1'-biphenyl][2-(2-aminoethyl)phenyl)]palladium(II), 2-(Di-tert-butylphosphino)-2',4',6'-triisopropyl-1,1'-biphenyl][2-2-aminoethyl)phenyl), potassium tert-butoxide |
| 24 | 5-(2-Methoxyethyl)-6-methyl-2-{2-[(1-methyl-1H-pyrazol-5-yl)amino]pyridin-4-yl}-5,6-dihydro-4H-thieno[2,3-c]pyrrol-4-one | 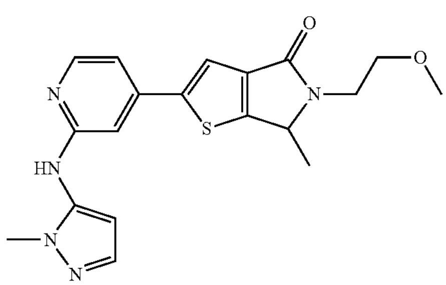 | 384 (M + 1) | Cesium carbonate |

EXAMPLE 25

5-(2-Methoxyethyl)-2-{2-[(1-methyl-1H-pyrazol-5-yl)amino]pyridin-4-yl}-5,6-dihydro-4H-thieno[2,3-c]pyrrol-4-one

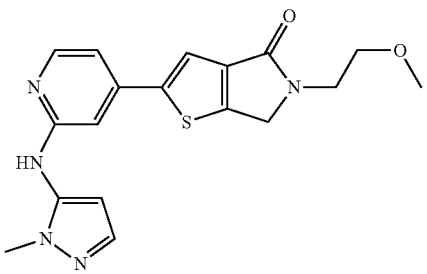

Sparge a solution of 4-chloro-N-(2-methylpyrazol-3-yl)pyridin-2-amine (2.0 g, 9.6 mmol), bis(pinacolato)diboron (4.9 g, 19 mmol), potassium acetate (3.3 g, 34 mmol), 2-dicyclohexylphosphino-2',4',6'-triisopropylbiphenyl (228 mg, 0.48 mmol) and chloro(2-dicyclohexylphosphino-2',4',6'-triisopropyl-1,1'-biphenyl)[2-(2'-amino-1,1'-biphenyl)]palladium(II) (226 mg, 0.29 mmol) in absolute EtOH (170 mL) with nitrogen for two minutes. Heat the mixture at 60° C. for 2.5 hours. Increase the heat to 75° C. and heat overnight. Cool the reaction to room temperature and use the product as a solution. Combine a portion of this solution (40 mL) with 2-bromo-5-(2-methoxyethyl)-6H-thieno[2,3-c]pyrrol-4-one (300 mg, 1.1 mmol), potassium phosphate tribasic N-hydrate (692 mg, 3.26 mmol) in additional EtOH (24 mL). Heat the reaction at 75° C. for one hour. Treat the mixture with water (9 mL) and heat the reaction at 75° C. overnight. Add tetrakis(triphenylphosphine)palladium(0) (200 mg) and continue heating for six hours. Cool the reaction to room temperature and dilute the reaction with DCM. Wash the organic solution with saturated NaCl. Back extract the aqueous solution with additional DCM. Combine the organic extracts and dry over sodium sulfate. Filter the mixture and concentrate the filtrate under reduced pressure. Purify the residue by silica gel column chromatography by loading the product onto a 25 g loading column and eluting the column onto a 40 g column with a gradient from 0-5% MeOH in DCM to give the title compound 90 mg (23%). MS (m/z): 370 (M+1).

EXAMPLE 26

6,6-Dimethyl-2-{2-[(1-methyl-1H-pyrazol-5-yl)amino]pyridin-4-yl}-5,6-dihydro-4H-thieno[2,3-c]pyrrol-4-one

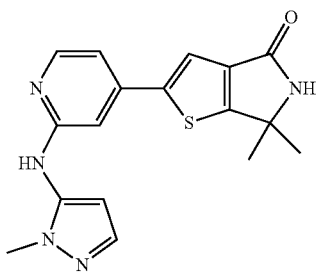

Treat a solution of tert-butyl 6,6-dimethyl-2-[2-[(2-methylpyrazol-3-yl)amino]-4-pyridyl]-4-oxo-thieno[2,3-c]pyrrole-5-carboxylate (120 mg, 0.27 mmol) in DCM (10 mL) with trifluoroacetic acid (5 mL). Stir the resulting mixture for two hours. Concentrate the reaction under reduced pressure and dissolve the residue in DCM. Wash the organic solution with saturated aqueous sodium bicarbonate. Separate the layers and back extract the aqueous layer with 10% MeOH in DCM. Combine the organic solutions and concentrate under reduced pressure. Purify the residue by silica gel column chromatography by loading the product onto a 5 g pre-column and eluting the pre-column onto a 40 g column with a gradient from 4-10% MeOH in EtOAc. Combine the appropriate fractions and concentrate under reduce pressure. Purify the residue by silica gel column chromatography by loading the product onto a 25 g pre-column and eluting the pre-column onto a 40 g column with a gradient from 0-10% MeOH in EtOAc. Combine the appropriate fractions and concentrate under reduce pressure to give the title compound 87 mg (94%). MS (m/z): 340 (M+1).

EXAMPLE 27

6-Ethyl-5-(2-methoxyethyl)-6-methyl-2-{2-[(1-methyl-1H-pyrazol-5-yl)amino]pyridin-4-yl}-5,6-dihydro-4H-thieno[2,3-c]pyrrol-4-one, Isomer 1

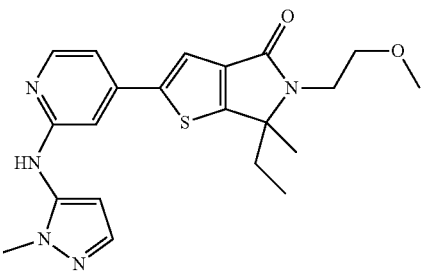

Purify 6-ethyl-5-(2-methoxyethyl)-6-methyl-2-{2-[(1-methyl-1H-pyrazol-5-yl)amino]pyridin-4-yl}-5,6-dihydro-4H-thieno[2,3-c]pyrrol-4-one (Example 20) by chiral chromatography. Chiralpak® IA; MP: 10% MeOH in ACN containing 0.2% isopropyl amine; Flow: 1.0 mL/min; UVW: 225 nm; 4.96 min, MS (m/z): 412 (M+1).

The following compounds are prepared essentially by the method of Example 27.

Alternate purification conditions are indicated.

TABLE 9

Examples 28-30

| Example No. | Compound Name | Structure | Conditions | Retention Time, MS (m/z): |
|---|---|---|---|---|
| 28 | 6-Ethyl-5-(2-methoxyethyl)-6-methyl-2-{2-[(1-methyl-1H-pyrazol-5-yl)aminolpyridin-4-yl{-5,6-dihydro-4H-thieno[2,3-c]pyrrol-4-one, Isomer 2 | Isomer 2 | Chiralpak ® IA; MP: 10% MeOH in ACN containing 0.2% isopropyl amine; Flow: 1.0 mL/min, 225 nM, | 7.012 min, 412 (M + 1) |
| 29 | 5-[2-Methoxypropyl]-6,6-dimethyl-2-{2-[(1-methyl-1H-pyrazol-5-yl)amino]pyridin-4-yl}-5,6-dihydro-4H-thieno[2,3-c]pyrrol-4-one. Isomer 1 | Isomer 1 | Chiralpak ® AS-H; MP: 40% isopropanol/CO$_2$ containing 0.2% isopropyl amine; Flow: 5.0 mL/min, 225 nM, | 1.23 min, 412 (M + 1) |
| 30 | 5-[2-Methoxypropyl]-6,6-dimethyl-2-{2-[ft-methyl-1H-pyrazol-5-yl)aminolpyridin-4-yl}-5,6-dihydro-4H-thieno[2,3-c]pyrrol-4-one Isomer 2 | Isomer 2 | Chiralpak ® AS-H; MP: 40% isopropanol/CO$_2$ containing 0.2% isopropyl amine; Flow: 5.0 mL/min, 225 nM, | 1.79 min, 412 (M + 1) |

X-Ray Powder Diffraction

The XRD patterns of crystalline solids are obtained on a Bruker D4 Endeavor X-ray powder diffractometer, equipped with a CuKa source ($\lambda$=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.853 and 26.774 degrees 2-theta.

X-Ray Powder Diffraction of Example 1, Crystalline Form 1

A prepared sample of Example 1 Crystalline Form 1 is characterized by an XRD pattern using CuKa radiation as having diffraction peaks (2-theta values) as described in Table 10 below, and in particular having peaks at 24.20 in combination with one or more of the peaks selected from the group consisting of 8.0°, 12.8°, 15.9°, 16.8°, and 19.5°; with a tolerance for the diffraction angles of 0.2 degrees.

TABLE 10

X-ray powder diffraction peaks of Example 1, Crystalline Form 1

| Peak | Angle (°2-Theta) +/- 0.2° | Relative Intensity (% of most intense peak) |
|---|---|---|
| 1 | 8.0 | 32 |
| 2 | 9.4 | 24 |
| 3 | 12.8 | 63 |
| 4 | 15.9 | 57 |
| 5 | 16.8 | 38 |
| 6 | 17.0 | 23 |
| 7 | 17.9 | 20 |
| 8 | 18.5 | 33 |
| 9 | 19.5 | 85 |
| 10 | 19.8 | 38 |
| 11 | 20.0 | 37 |
| 12 | 21.6 | 31 |
| 13 | 22.9 | 24 |
| 14 | 24.2 | 100 |
| 15 | 24.8 | 18 |
| 16 | 26.6 | 25 |

X-Ray Powder Diffraction of Example 1, Crystalline Form 2

A prepared sample of Example 1 Crystalline Form 2 is characterized by an XRD pattern using CuKa radiation as having diffraction peaks (2-theta values) as described in Table 11 below, and in particular having peaks at 18.5° in combination with one or more of the peaks selected from the group consisting of 8.5°, 9.2°, 16.5°, 20.3°, and 23.3°; with a tolerance for the diffraction angles of 0.2 degrees.

TABLE 11

X-ray powder diffraction peaks of Example 1, Crystalline Form 2

| Peak | Angle (°2-Theta) +/- 0.2° | Relative Intensity (% of most intense peak) |
|---|---|---|
| 1 | 8.5 | 16 |
| 2 | 9.2 | 14 |
| 3 | 12.9 | 9 |
| 4 | 14.2 | 7 |
| 5 | 16.1 | 20 |
| 6 | 16.5 | 66 |
| 7 | 17.1 | 9 |
| 8 | 18.5 | 100 |
| 9 | 19.2 | 11 |
| 10 | 20.3 | 38 |
| 11 | 21.3 | 15 |
| 12 | 23.3 | 24 |
| 13 | 27.6 | 15 |
| 14 | 27.9 | 19 |

Several lines of evidence indicate that processes involved in tumor initiation, growth and progression are mediated by activation of one or more signaling pathways in cancer cells. The mitogen-activated protein kinase (MAPK) pathway is a key regulator of cellular proliferation and survival. ERK is a downstream member of this pathway and plays a central role in transmitting extracellular signals from activated receptor tyrosine kinases (RTKs) such as EGFR, FGFR, PDGFR, VEGFR etc. This pathway is a three tiered kinase cascade consisting of the RAF, MEK and ERK (extracellular signal regulated kinase) kinases and the activation of this pathway begins with activation of RAS, a small GTPase. Activation of RAS leads to the recruitment of RAF, a serine/threonine kinase and its activation. Activated RAF then phosphorylates and activates MEK1/2, which in turn phosphorylates and activates ERK1/2. When activated, ERK1/2 phosphorylates several downstream cytoplasmic and nuclear targets involved in cell proliferation, growth, survival and EMT (epithelial-to-mesenchymal transition).

The RAS/MAPK pathway is one of the most important pathways for cell proliferation and it is believed that this pathway is frequently activated in ~30% of all human cancers. Constitutive MAPK pathway activation can result from activating mutations in RAS, BRAF, MEK1, loss of the tumor suppressor NF1 or upstream activation mediated by mutations, amplifications or ligand mediated activation of RTKs. All three RAS family genes (KRAS, NRAS and HRAS) have been shown to be somatically mutated in several cancers including colorectal, melanoma, lung and pancreatic cancer, most commonly as a result of single point mutations at codons 12, 13, and 61. These mutations cause constitutive activation of RAS which is accompanied by increased ERK1/2 activity and growth signaling. Mutations in codons 12, 13 and 61 of KRAS confer resistance to compounds and monoclonal antibodies inhibiting EGFR. KRAS mutations are found in 30% of lung cancers, 90% of pancreatic cancers, 10% of gastric cancers and 50% of colorectal cancers. NRAS mutations were detected in about 10-25% of melanoma. In addition, RAS mutations (HRAS, KRAS, and NRAS) have been identified in ~55-60% of thyroid cancers. Somatic point mutations in BRAF occur in about 8% of human tumors, most frequently in melanoma (60%), colorectal (10%) and thyroid cancers (50%). In melanoma, all BRAF mutations appear to be within kinase domain and a single substitution (T->A, V600E) accounts for 80% of the mutations. BRAF mutations are found, with rare exceptions, in a mutually exclusive pattern with RAS mutations, suggesting that these genetic alterations activate common downstream effectors.

Biological Assays

The following assays demonstrate that the exemplified compounds of the present invention are inhibitors of ERK1 and ERK2 kinase activity. The results of the following assays also demonstrate that the exemplified compounds of the present invention inhibit ERK signaling in cancer cells. Additionally, the Compound of Example 1 demonstrates ERK pathway target inhibition in certain xenograft tumor models of cancer. Furthermore, the compound of Example 1 inhibits tumor growth in certain xenograft tumor models of cancer.

ERK1 Kinase Assay

The purpose of this assay is to measure the ability of compounds to inhibit ERK1 kinase activity. Perform the ERK1 kinase assay in vitro using a TR-FRET assay. Start reactions (12.5 µL) by adding 5 CL of ERK1 enzyme (Invitrogen, #PR5254B, final concentration 100 ng/mL) plus substrate GFP-ATF2 (Invitrogen, # PV4445, final concentration 0.2 µM), 5 µL of ATP solution (Invitrogen, # PV3227, final concentration 10 µM) prepared in kinase buffer (50 mM Hepes pH 7.4, 5 mM $MgCl_2$, 0.1 mM EGTA, 0.01% Triton X-100, 1 mM DTT) and 2.5 L of testing compounds in DMSO solution (final 4%, v/v) in a 384-well PROXI-PLATE™ (Perkin Elmer, #GRN6260). Incubate the reaction mixture at room temperature for 60 minutes. Stop the reaction by addition of 12.5 µL of stop buffer (10 mM EDTA, 2 nM Tb-anti-pATF2 (pThr71) antibody, Invitrogen, #PV4448) in TR-FRET dilution buffer (Invitrogen, # PV3574). Incubate the plates at room temperature for an additional 60 minutes and read on an ENVISION® (PerkinElmer) plate reader at the excitation wavelength 340 nm. Calculate the TR-FRET ratio by dividing the GFP acceptor emission signal (at 520 nm) by the Tb donor emission signal (at 495 nm). Calculate percent inhibition using compound treated wells relative to on-plate Max (DMSO control) and Min (No enzyme added) control wells TR-FRET ratio data {% inhibition=100−[(test compound−median Min)/(median Max−median Min)×100]}). Test all compounds at 10 concentrations (20 μM to 0.001 μM) using a 1:3 dilution scheme. Derive Abs_$IC_{50}$ values by fitting percent inhibition and ten-point concentration data to a 4-parameter nonlinear logistic equation (equation 205) using ACTIVITYBASE® 7.3 (ID Business Solutions Limited).

The exemplified compounds within the scope of the invention are tested in this assay substantially as described above. The results of this assay demonstrate that all of the exemplified compounds inhibit ERK1 kinase activity, with $IC_{50}$ values less than 0.15 μM. For example, the compound of Example 1 has an $IC_{50}$ value of 1.50 nM (±0.608, n=16).

ERK2 Kinase Assay

The purpose of this assay is to measure the ability of compounds to inhibit ERK2 kinase activity. Perform the ERK2 kinase assay in vitro using a TR-FRET assay. Start all reactions (12.5 μL) by adding 5 L of ERK2 enzyme (Invitrogen, #PV3595B, final conc 50 ng/mL) plus substrate GFP-ATF2 (Invitrogen, #PV4445, final conc 0.2 μM), 5 L of ATP solution (Invitrogen, #PV3227, final conc 10 μM) prepared in kinase buffer (50 mM Hepes pH 7.4, 5 mM $MgCl_2$, 0.1 mM EGTA, 0.01% Triton X-100, 1 mM DTT) and 2.5 μL of testing compounds in DMSO solution (final 4%, v/v) in a 384-well PROXIPLATE™ (Perkin Elmer, #GRN6260). Incubate reactions at room temperature for 60 minutes. Stop reactions by addition of 12.5 L of stop buffer (10 mM EDTA, 2 nM Tb-anti-pATF2 (pThr71) antibody, Invitrogen, #PV4448) in TR-FRET dilution buffer (Invitrogen, # PV3574). Incubate the plates at room temperature for an additional 60 minutes and read ON ENVISION® (PerkinElmer) plate reader at the excitation wavelength of 340 nm. Calculate a TR-FRET ratio by dividing the GFP acceptor emission signal (at 520 nm) by the Tb donor emission signal (at 495 nm). Calculate percent inhibition using compound wells relative to on-plate Max (DMSO control) and Min (No enzyme added) control wells TR-FRET ratio data {% inhibition=100−[(test compound−median Min)/(median Max−Min)×100]}. Test all compounds at concentrations (20 μM to 0.001 μM) using a 1:3 dilution scheme. Derive Abs_IC50 values by fitting percent inhibition and ten-point concentration data to a 4-parameter nonlinear logistic equation (equation 205) using ACTIVITYBASE 7.3 (ID Business Solutions Limited).

The exemplified compounds within the scope of the invention are tested in this assay substantially as described above. The results of this assay demonstrate that all of the exemplified compounds inhibit ERK2 kinase activity, with $IC_{50}$ values less than 0.15 μM. For example, the compound of Example 1 has an $IC_{50}$ value 1.93 nM (±0.682, n=17).

ERK1/2 Cell Mechanistic Assay (pRSK1 Alphascreen Assay)

The purpose of this assay is to measure the ability of compounds to inhibit ERK signaling in cancer cells in vitro.

Carry out the pRSK1 Alphascreen assay using the HCT116 colorectal cancer cell line (ATCC, # CCL-247). Routinely culture HCT116 cells in Dulbecco's Modified Eagle's Medium (DMEM) (Hyclone, #SH30022) growth medium containing 5% Fetal Bovine Serum (FBS) (Gibco, #16000-044) in T-150 flasks and incubate in a 5% $CO_2$ incubator at 37° C. Harvest cells when they become confluent and freeze in freezing medium at $1 \times 10e^7$ cells/mL as "assay ready frozen cells" and store in liquid nitrogen. To run the assay, plate 40,000 HCT116 cells/well in a 96-well tissue culture plate and incubate at 37° C. in a 5% $CO_2$ incubator overnight. Test compounds at 10 concentrations starting at a 20 μM top concentration and utilize a 1:3 dilution scheme (20 μM to 0.001 μM) with a final DMSO concentration of 0.5% (v/v). Add compounds in 20 μL serum free growth medium and incubate at 37° C. for two hours. Remove growth medium and add 50 μL of 1× lysis buffer [Cell Signaling Technology, #9803] containing 1×holt protease and phosphatase inhibitor cocktail [Thermo, #78441] to each well and incubate at room temperature for 10 minutes on a shaker. Transfer 4 μL of cell lysate from each well to respective wells in a 384 well assay plate [Perkin Elmer, #6006280] and add 5 μL of reaction mix [2000 parts 1×assay buffer (Perkin Elmer, #A1000), 1 part biotin-RSK1 antibody (Santa Cruz, # sc-231-B-G), 4 parts pRSK1 antibody (Abcam, # ab32413), 35 parts acceptor beads (Perkin Elmer, #6760617R)]. Seal the plate with foil plate seal (Beckman Coulter, #538619) and incubate at room temperature for two hours. Add 2 μL of donor beads [20 parts 1× assay buffer, 1 part donor beads] to each well and seal the plate with clear plate seal (Applied Biosystems, #4311971) and incubate at room temperature in the dark for two hours. Measure the fluorescence intensity in each well by reading the plates in ENVISION® (PerkinElmer) plate reader. Derive the Rel $IC_{50}$ values by fitting percent pRSK1 inhibition [% inhibition=100−[(test compound−median Min)/(median Max−median Min)×100] and ten-point concentration data to a 4-parameter nonlinear logistic equation (Abase equation 205) using ACTIVITYBASE® 7.3 (ID Business Solutions Limited).

The exemplified compounds within the scope of the invention are tested in this assay substantially as described above. The results of this assay demonstrate that all of the exemplified compounds inhibit ERK substrate (RSK) phosphorylation in tumor cells, with $IC_{50}$ values less than 3 μM. For example, the compound of Example 1 has an $IC_{50}$ value of 0.261 μM (±0.0876, n=10).

In Vivo Target Inhibition (IVTI) Assay (pRSK1 ELISA Assay)

The purpose of this assay is to measure the ability of a test compound to inhibit ERK1/2 substrate phosphorylation in an animal model. Implant female athymic nude mice (22-25 g) from Harlan Laboratories with $5 \times 10e^6$ HCT116 colorectal cancer cells (ATCC, # CCL-247) subcutaneously in the right flank region in 200 μL of 1:1 Hank's Balanced Salt Solution (HBSS)+Matrigel solution. Measure tumor growth and body weight twice per week beginning the seventh day after the implantation. When tumor sizes reach 300-500 $mm^3$, randomize animals and group into groups of five animals. Dose animals with either compound at an appropriate dose in a compound specific vehicle or vehicle alone orally (vehicle: 1% HEC/0.25% Tween 80/0.05% Antifoam) and collect tumors and blood at desired time intervals after dosing. Sacrifice animals using isoflurane anesthesia plus cervical dislocation. Flash freeze tumors and store at −80° C. until processing for pRSK1 levels by ELISA assay. Collect blood in EDTA tubes and spin down for plasma and freeze at −80° C. in a 96-well plate. Determine compound exposures using standard methods.

Pulverize tumors in liquid nitrogen and lyse in 1× lysis buffer (MSD, #R60TX-3) containing 1× halt protease & phosphatase inhibitor cocktail (Thermo Scientific, #0861281), 1 mM phenylmethanesulfonyl fluoride (PMSF) (Sigma, #93482-50ML-F) and 1 μM sodium metavanadate (Sigma, #590088) using Matrix D beads (MP Biomedical, #6913-500) in a FastPrep-24™ Cell Disrupter machine (MP Biomedical) in a cold room (4° C.). Transfer tumor lysates to fresh tubes after spinning at 14000 rpm for 20 minutes at 4° C. Determine protein concentration of tumor or cell lysates using Pierce BCA Protein Assay Kit (cat#23225, Thermo Scientific). This kit contains three main components—(1) BCA Reagent A, containing sodium carbonate, sodium bicarbonate, bicinchoninic acid and sodium tartarate in 0.1 M sodium hydroxide, (2) BCA Reagent B, containing 4% cupric sulfate, and (3) Albumin standard ampules, containing 2 mg/mL in 0.9% saline and 0.05% sodium azide. In a 96-well plate, add bovine serum albumin protein standard for a concentration range of 20-2000 ug/mL in 25 μL in duplicate wells to generate a standard curve. Add cell or tumor lysates diluted in 25 μL 1×PBS to duplicate test wells. Prepare working BCA reagent by adding 2% Reagent B to Reagent A (2 mL of B+98 mL of A), mix well and add 200 μL to each sample or standard. Mix well, cover the plate and incubate at 37° C. for 30 minutes. Cool plate to room temperature and measure the absorbance at or near 562 nm on a plate reader (Envision plate reader from Perkin Elmer). Subtract the average 562 nm absorbance measurement of the blank standard replicates from the 562 nm measurements of all other individual standard and unknown (cell or tumor lysate) sample replicates. Prepare a standard curve by plotting the average blank-corrected 562 nm measurement for each bovine serum albumin standard versus its concentration in μg/mL. Use the standard curve to determine the protein concentration of each unknown samples using curve-fit logarithms in Microsoft Excel. Freeze remaining tumor lysates at −80° C. Use once freeze-thawed tumor lysates to measure pRSK1 expression by sandwich ELISA.

Coat 96-well plates (Thermo, #15042) overnight at 4° C. with 40 ng of RSK1 goat antibody (Santa Cruz, # sc-231-G) and incubate at room temperature for one hour and then at 4° C. overnight. Wash plates three times with 300 μL of PBST (1× phosphate buffered saline (PBS) containing 0.05% Tween-20), block with 100 μL per well of blocking buffer (Thermo Scientific, #37532) and incubated at room temperature for two hours. Wash plates three times with 300 μL PBST and transfer 20 μg of tumor lysate to each well and incubate at 4° C. overnight. Wash plates three times with 300 μL PBST and incubate with 100 L of pRSK1 (T359/S363) rabbit antibody (1:1000 dilution in blocking buffer) at room temperature for four hours. Wash plates three times with 300 μL PBST and incubate with 100 μL anti-rabbit HRP-conjugated secondary antibody (GE Healthcare UK, #NA934V; diluted 1:10000 in blocking buffer) Incubate at room temperature for one hour. Wash plates three times with 300 μL of PBST, add 100 μL of SUPERSIGNAL® ELISA Femto maximum sensitivity substrate (Thermo, #37075) and incubate on a shaker for one minute. Determine the luminescence signal using an ENVISION® plate reader. Determine the pRSK1 level in each tumor lysate by considering tumor lysates from animals treated with vehicle (vehicle: 1% HEC/0.25% Tween 80/0.05% Antifoam) alone as 100%. Analyze each sample in duplicate and use average numbers for calculations. Calculate $TED_{50}$ using Excel and XL Fit.

A compound within the scope of the invention is tested in this assay substantially as described above. The results of this assay demonstrate that the Compound of Example 1 inhibits RSK1 phosphorylation in a tumor xenograft model. For example, the compound of Example 1 has a $TED_{50}$ value of 12 mg/kg.

Xenograft Tumor Models

The purpose of this assay is to measure reduction in tumor volume in response to test compound administration. Expand human colorectal cancer cells HCT116 (ATCC, #CCL-247) or human non-small cell lung cancer cells NCI-H358 (ATCC, # CRL-5807) in culture, harvest and inject $5×10e^6$ cells in 200 μL of 1:1 HBSS+matrigel solution subcutaneously on to the rear right flank of female athymic nude mice (22-25 gm, Harlan Laboratories). Expand human pancreatic cancer cells SW1990 (ATCC, # CRL-2172) in culture, harvest and inject $2×10e^6$ cells in 200 μL of 1:1 HBSS+matrigel solution subcutaneously on to the rear right flank of female athymic nude mice (22-25 gm, Harlan Laboratories). Expand human pancreatic cancer cells MIA PACA-2 (ATCC, # CRL-1420) or human non-small cell lung cancer cells A549 (ATCC, # CCl-185) in culture, harvest and inject $5×10e^6$ cells in 200 μL of 1:1 HBSS+ matrigel solution subcutaneously on to the rear right flank of female CB-17 SCID mice (22-25 gm, Charles River Laboratories International Inc.). Expand human melanoma cells A-375 (ATCC, # CRL-1619) in culture, harvest and inject $5×10e^6$ cells in 200 μL of 1:1 HBSS+matrigel solution subcutaneously on to the rear right flank of female NIH nude rats (140-160 gm, Taconic Farms). Measure tumor growth and body weight twice per week beginning the seventh day after the implantation. When tumor sizes reach 200-400 $mm^3$, randomize animals and group into groups of eight to ten animals. Prepare test compound in an appropriate vehicle (vehicle: 1% HEC/0.25% Tween 80/0.05% Antifoam) and administer by oral gavage for 14 to 28 days. Tumor response is determined by tumor volume measurement performed twice a week during the course of treatment.

A compound within the scope of invention is tested in this assay run substantially as above. The compound of Example 1 is found to have delta T/C % values as provided in Table 12 below. These results indicate that the compound of Example 1 demonstrates significant anti-tumor activity in several human cancer xenograft models including HCT116, MIA PACA-2, CALU-6, SW1990, NCI-H358, A549 and A-375.

TABLE 12

Xenograft models

| Tumor Model | Dose (mg/kg) | Schedule | p-value | Delta T/C (%) | Regression (%) |
| --- | --- | --- | --- | --- | --- |
| HCT116 | 10 | BID | 0.023* | 55 | NA |
| HCT116 | 25 | BID | <0.001* | 89 | NA |
| HCT116 | 50 | QD | <0.001* | 83 | NA |
| HCT116 | 50 | BID | <0.001* | NA | −31 |
| HCT116 | 75 | QD | <0.001* | 98 | NA |
| MIA PACA-2 | 10 | BID | <0.001* | 76 | NA |
| MIA PACA-2 | 25 | QD | <0.001* | 74 | NA |
| MIA PACA-2 | 25 | BID | <0.001* | NA | −15 |
| MIA PACA-2 | 50 | QD | <0.001* | 97 | NA |
| MIA PACA-2 | 50 | BID | <0.001* | NA | −72 |
| MIA PACA-2 | 75 | QD | <0.001* | NA | −39 |

TABLE 12-continued

Xenograft models

| Tumor Model | Dose (mg/kg) | Schedule | p-value | Delta T/C (%) | Regression (%) |
|---|---|---|---|---|---|
| CALU-6 | 10 | BID | 0.013* | 44 | NA |
| CALU-6 | 25 | QD | 0.010* | 46 | NA |
| CALU-6 | 25 | BID | <0.001* | NA | −10 |
| CALU-6 | 50 | QD | <0.001* | 92 | NA |
| CALU-6 | 50 | BID | <0.001* | NA | −75 |
| CALU-6 | 75 | QD | <0.001* | NA | −38 |
| SW1990 | 10 | BID | 0.364 | 24 | NA |
| SW1990 | 30 | BID | 0.005* | 64 | NA |
| NCI-H358 | 25 | BID | <0.001* | NA | −13 |
| NCI-H358 | 50 | BID | <0.001* | NA | −35 |
| A549 | 10 | BID | 0.471 | 13 | NA |
| A549 | 30 | BID | <0.001* | 66 | NA |
| A-375 | 3 | QD | 0.852 | 10 | NA |
| A-375 | 3 | BID | <0.001* | NA | −60 |
| A-375 | 15 | BID | <0.001* | NA | −47 |

Analysis for tumor volume is based on Log 10 and SpatialPower covariance structure.
*significant (p < 0.05)
NA: Not applicable
Delta T/C % is calculated when the endpoint tumor volume in a treated group is at or above baseline tumor volume. The formula is $100*(T - T_0)/(C - C_0)$, where T and C are mean endpoint tumor volumes in the treated or control group, respectively. $T_0$ and $C_0$ are mean baseline tumor volumes in those groups.
Regression % is calculated when the endpoint volume is below baseline. The formula is $100*(T - T_0)/T_0$. Where $T_0$ is the mean baseline tumor volume for the treated group. For HCT116, MIA PACA-2, CALU-6, SW 1990, NCI-H358, A549 and A-375 models, grand mean of all groups from baseline (randomization) at day 17, day 18, day 15, day 21, day 29, day 20, and day 24 respectively was used to compute % change of T/C.

We claim:

1. A compound of the formula:

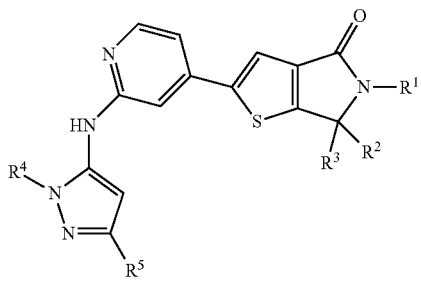

wherein:
$R^1$ is hydrogen, 2-methoxyethyl, 2-(cyclopropoxy)ethyl, 2-hydroxyethyl, 2-(2,2-difluoroethoxy)ethyl, 2-(trideuteriomethoxy)ethyl, 2-(trifluoromethoxy)ethyl, 2-methoxypropyl, (2R)-2-methoxypropyl, or (2S)-2-methoxypropyl;
$R^2$ and $R^3$ are independently hydrogen, methyl, or ethyl or $R^2$ and $R^3$ can be taken together to form cyclopropyl or cyclopentyl;
$R^4$ is hydrogen, methyl, ethyl, isopropyl, cyclopropyl, difluoromethyl, 2-fluoroethyl, 2,2-difluoroethyl, 2,2,2-trifluoroethyl, or 2-methoxyethyl; and
$R^5$ is hydrogen, methyl, or cyclopropyl;
or a pharmaceutically acceptable salt thereof.

2. The compound or salt according to claim 1 wherein $R^2$ and $R^3$ are methyl.

3. The compound or salt according to claim 2 wherein $R^1$ is 2-methoxyethyl.

4. The compound or salt according to claim 3 wherein $R^4$ is methyl.

5. The compound or salt according to claim 3 wherein $R^5$ is hydrogen.

6. The compound or salt according to claim 4 which is 5-(2-methoxyethyl)-6,6-dimethyl-2-{2-[(1-methyl-1H-pyrazol-5-yl)amino]pyridin-4-yl}-5,6-dihydro-4Hthieno[2,3-c]pyrrol-4-one.

7. The compound according to claim 6 which is 5-(2-methoxyethyl)-6,6-dimethyl-2-{2-[(1-methyl-1H-pyrazol-5-yl)amino]pyridin-4-yl}-5,6-dihydro-4Hthieno[2,3-c]pyrrol-4-one.

8. A pharmaceutical composition comprising a compound of the formula:

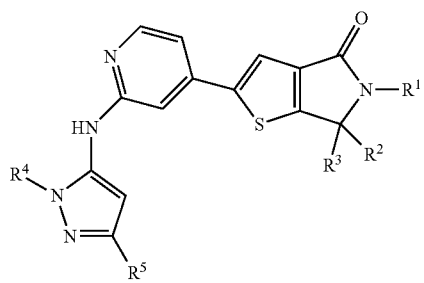

wherein:
$R^1$ is hydrogen, 2-methoxyethyl, 2-(cyclopropoxy)ethyl, 2-hydroxyethyl, 2-(2,2-difluoroethoxy)ethyl, 2-(trideuteriomethoxy)ethyl, 2-(trifluoromethoxy)ethyl, 2-methoxypropyl, (2R)-2-methoxypropyl, or (2S)-2-methoxypropyl;
$R^2$ and $R^3$ are independently hydrogen, methyl, or ethyl or $R^2$ and $R^3$ can be taken together to form cyclopropyl or cyclopentyl;
$R^4$ is hydrogen, methyl, ethyl, isopropyl, cyclopropyl, difluoromethyl, 2-fluoroethyl, 2,2-difluoroethyl, 2,2,2-trifluoroethyl, or 2-methoxyethyl; and
$R^5$ is hydrogen, methyl, or cyclopropyl;
or a pharmaceutically acceptable salt thereof,
and a pharmaceutically acceptable carrier, diluent, or excipient.

9. A method of treating cancer wherein the cancer is selected from the group consisting of melanoma, colorectal cancer, pancreatic cancer, and non-small cell lung cancer, comprising administering to a patient in need thereof, an effective amount of a compound of the formula:

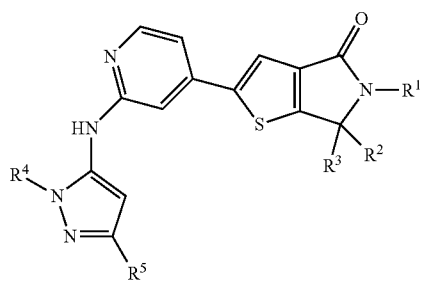

wherein:
$R^1$ is hydrogen, 2-methoxyethyl, 2-(cyclopropoxy)ethyl, 2-hydroxyethyl, 2-(2,2-difluoroethoxy)ethyl, 2-(trideuteriomethoxy)ethyl, 2-(trifluoromethoxy)ethyl, 2-methoxypropyl, (2R)-2-methoxypropyl, or (2S)-2-methoxypropyl;
$R^2$ and $R^3$ are independently hydrogen, methyl, or ethyl or $R^2$ and $R^3$ can be taken together to form cyclopropyl or cyclopentyl;

R⁴ is hydrogen, methyl, ethyl, isopropyl, cyclopropyl, difluoromethyl, 2-fluoroethyl, 2,2-difluoroethyl, 2,2,2-trifluoroethyl, or 2-methoxyethyl; and R⁵ is hydrogen, methyl, or cyclopropyl;

or a pharmaceutically acceptable salt thereof.

10. The method according to claim 9, wherein the cancer is colorectal cancer.

11. The method according to claim 9, wherein the cancer is pancreatic cancer.

12. The method according to claim 9, wherein the cancer is non-small cell lung cancer.

* * * * *

UNITED STATES PATENT AND TRADEMARK OFFICE
CERTIFICATE OF CORRECTION

PATENT NO. : 9,879,029 B2
APPLICATION NO. : 15/529641
DATED : January 30, 2018
INVENTOR(S) : Guillermo S. Cortez et al.

Page 1 of 1

It is certified that error appears in the above-identified patent and that said Letters Patent is hereby corrected as shown below:

On the Title Page

Under "Attorney, Agent, or Firm" (74), please delete "Dannica" and insert --Danica--, therefor.

In the Claims

In Column 62, Line 3, in Claim 6, please delete "4Hthieno" and insert --4H-thieno--, therefor.

In Column 62, Line 7 (approximately), in Claim 7, please delete "4Hthieno" and insert --4H-thieno--, therefor.

Signed and Sealed this
Twenty-seventh Day of March, 2018

Andrei Iancu
*Director of the United States Patent and Trademark Office*